(12) United States Patent
Vaughan et al.

(10) Patent No.: US 8,067,564 B2
(45) Date of Patent: Nov. 29, 2011

(54) METHODS OF OBTAINING A SPECIFIC BINDING MEMBER THAT BINDS EOTAXIN

(75) Inventors: Tristan John Vaughan, Cambridge (GB); Alison Jane Wilton, Cambridge (GB); Stephen Smith, Cambridgeshire (GB); Sarah Helen Main, Royston (GB)

(73) Assignee: MedImmune Limited, Cambridge (GB)

( * ) Notice: Subject to any disclaimer, the term of this patent is extended or adjusted under 35 U.S.C. 154(b) by 432 days.

(21) Appl. No.: 11/958,210

(22) Filed: Dec. 17, 2007

(65) Prior Publication Data

US 2008/0182319 A1    Jul. 31, 2008

Related U.S. Application Data

(62) Division of application No. 10/220,418, filed as application No. PCT/GB01/00927 on Mar. 2, 2001, now Pat. No. 7,323,311.

(60) Provisional application No. 60/187,246, filed on Mar. 3, 2000.

(51) Int. Cl.
  *C07H 21/04* (2006.01)
  *C12N 5/00* (2006.01)
  *C07K 17/00* (2006.01)

(52) U.S. Cl. ............... 536/23.53; 435/325; 435/326; 435/328; 435/335; 435/344.1; 435/346

(58) Field of Classification Search .................. None
See application file for complete search history.

(56) References Cited

U.S. PATENT DOCUMENTS

| | | | |
|---|---|---|---|
| 4,816,567 A * | 3/1989 | Cabilly et al. | 530/387.3 |
| 5,993,814 A | 11/1999 | Williams et al. | 424/145.1 |
| 6,031,080 A | 2/2000 | Williams et al. | 530/351 |
| 6,403,782 B1 | 6/2002 | Luster et al. | 536/23.5 |
| 6,946,546 B2 | 9/2005 | Vaughan et al. | 530/387.3 |
| 7,265,201 B1 * | 9/2007 | Ponath et al. | 530/324 |
| 7,323,311 B2 | 1/2008 | Vaughan et al. | 435/7.1 |
| 7,597,889 B1 * | 10/2009 | Armour et al. | 424/133.1 |

FOREIGN PATENT DOCUMENTS

| | | |
|---|---|---|
| EP | 0 546 634 | 6/1993 |
| GB | 2 350 612 | 12/2000 |
| WO | WO 91/07492 | 5/1991 |
| WO | WO 93/02190 | 2/1993 |
| WO | WO 97/00960 | 1/1997 |
| WO | WO 97/12914 | 4/1997 |
| WO | WO 99/10534 | 3/1999 |
| WO | WO 01/14424 | 3/2001 |
| WO | WO 02/02640 | 1/2002 |

OTHER PUBLICATIONS

Rudikoff et al. PNAS 1982 vol. 79, pp. 1979-1983.*
Rader et al. PNAS. 1998. 95:8910-8915.*
Cossins et al. Protein Expression and Purification 51 (2007) 253-259.*
Holt et al. Trends in Biotechnology vol. 21 No. 11 Nov. 2003. pp. 484-490.*
Colby et al. J. Mol. Biol. (2004) 342:901-912.*
van den Beucken et al. J. Mol. Biol. (2001) 310:591-601.*
Reiter et al. J. Mol. Biol. (1999) 290:685-698.*
Marks et al. Biotechnology BioTechnology 10 (1992) pp. 779-783.*
Xu et al. Immunity vol. 13, 37-45. Jul. 2000.*
Gonzalo et al., "Eosinophil Recruitment to the Lung in a Murine Model of Allergic Inflammation—The Role of T Cells, Chemokines, and Adhesion Receptors," *J. Clin. Invest.* 98(10):2332-2345, 1996.
Humbles et al., "Kinetics of Eotaxin Generation and Its Relationship to Eosinophil Accumulation in Allergic Airways Disease: Analysis in a Guinea Pig Model In Vivo," *J. Exp. Med.* 186(4):601-612, 1997.
Jackson et al., "Antigen specificity and tumour targering efficiency of a human carcinoembryonic antigen-specific scFv and affinity-matured derivatives," *British Journal of Cancer* 78(2):181-188, 1998.
Main et al., "A Potent Human Anti-Eoxtaxinl Antibody, CAT-213: Isolation by Phage Display and in Vitro and in Vivo Efficacy," *The Journal of Pharmacology and Experimental Therapeutics* 319(3):1395-1404, 2006.
Bensimon, C. et al., "Human lupus anti-DNA autoantibodies undergo essentially primary V$\chi$ gene rearrangements," *The EMBO Journal* 13(13):2951-2962, 1994.
Ewert, S. et al., "Stability improvement of antibodies for extracellular and intracellular applications: CDR grafting to stable frameworks and structure-based framework engineering," *Methods* 34:184-199, 2004.
Garcia-Zepeda, E. et al., "Human eotaxin is a specific chemoattractant for eosinophil cells an provides a new mechanism to explain tissue eosinophila," *Nat. Med.* 4:449-456, 1996.
Genbank Acc. No. BAA08370 Eotaxin (Internet website—ncbi.nlm. nih.gov.), p. 1 May 2, 2003.
Griffiths-Johnson, D. et al., "The Chemokine, Eotaxin, Activates Guinea-Pig Eosinophils in vitro and Causes Their Accumulation into the Lung in vivo," *Biochemical and Biophysical Research Communications* 197(3):1167-1172, 1993.
Harlow, E. et al., "Antibodies: A Laboratory Manual," 1988 by Cold Spring Harbor Laboratory, pp. 560-562.
Jose, P. et al., "Eotaxin: A Potent Eosinophil Chemoattractant Cytokine Detected in a Guinea Pig Model of Allergic Airways Inflammation," *J. Exp. Med.* 179:881-887, 1994.
Jose, P. et al., "Eotaxin: Cloning of an Eosinophil Chemoattractant Cytokine and Increased mRNA Expression in Allergen-Challenged Guinea-Pig Lungs," *Biochemical and Biophysical Research Communications* 205(1):788-794, 1994.
Kitaura, M. et al., "Molecular Cloning of Human Eotaxin, an Eosinophil-selective CC Chemokine, and Identification of a Specific Eosinophil Eotaxin Receptor, CC Chemokine Receptor 3," *JBC* 271(13):7725-7730, 1996.

(Continued)

*Primary Examiner* — Chun Dahle

(57) ABSTRACT

Specific binding members directed to eotaxin-1, in particular human antibodies and antibody fragments against human eotaxin-1 and especially those which neutralize eotaxin-1 activity. The antibodies VH and/or VL domain of the scFv fragment herein termed CAT-212 and of the IgG4 antibody herein termed CAT 213. One or more complementary determining regions (CDRs) of the CAT-212/-213 VH and/or VL domains, especially VH CRD3 in other antibody framework regions. Compositions containing specific binding members, and their use in methods of inhibiting or neutralizing eotaxin, including methods of treatment of the human or animal body by therapy.

18 Claims, 14 Drawing Sheets

OTHER PUBLICATIONS

Li, Y. et al., "Three-Dimensional Structures of the Free and Antigen-Bounds Fab from Monoclonal Antilysozyme Antibody HyHEL-63," *Biochemistry 39*:6296-6309, 2000.

Nakajima, T. et al., "Intracellular localization and release of eotaxin from normal eosinophils," *FEBS Letters 434*:226-230, 1998.

Pech, M. et al., "Organization and Evolution of a Gene Cluster for Human Immunoglobulin Variable Regions of the Kappa Type," *J. Mol. Biol. 176*:189-204, 1984.

Ponath, P. et al., "Cloning of the Human Eoshinophil Chemoattractant, Eotaxin," *J. Clin. Invest. 97*(3):604-612, 1996.

* cited by examiner

METHODS OF OBTAINING A SPECIFIC BINDING MEMBER THAT BINDS EOTAXIN

CROSS-REFERENCES TO RELATED APPLICATIONS

This application is a divisional of U.S. application Ser. No. 10/220,418, filed Jan. 9, 2003 now U.S. Pat. No. 7,323,311, now allowed, which is a national stage entry of International Application No. PCT/GB01/00927, filed Mar. 2, 2001 which claims the priority benefit of U.S. Provisional Patent Application No. 60/187,246, filed Mar. 3, 2000. The contents of each of these patent applications is incorporated herein by reference in its entirety.

STATEMENT REGARDING SEQUENCE LISTING

The Sequence Listing associated with this application is provided in text format in lieu of a paper copy, and is hereby incorporated by reference into the specification. The name of the text file containing the Sequence Listing is 480231_405D1_SEQUENCE_LISTING.txt. The text file is 7 KB, was created on Mar. 28, 2008, and is being submitted electronically via EFS-Web.

The present invention relates to specific binding members directed to eotaxin-1, in particular human antibodies against human eotaxin-1 and especially those which neutralise eotaxin-1 activity. Preferred embodiments of the present invention employ the antibody VH and/or VL domain of the scFv fragment herein termed CAT-212 and of the IgG4 antibody herein termed CAT-213. Further preferred embodiments employ one or more complementarity determining regions (CDRs) of the CAT-212/-213 VH and/or VL domains, especially VH CDR3 in other antibody framework regions. Further aspects of the present invention provide for compositions containing specific binding members of the invention, and their use in methods of inhibiting or neutralising eotaxin, including methods of treatment of the human or animal body by therapy.

Eotaxin-1 is a chemoattractant protein that binds to a specific receptor, CCR3, which is expressed predominantly on eosinophils. An anti-eotaxin-1 antibody may be used to inhibit eosinophilia and the recruitment of eosinophils to sites of inflammation. In one embodiment, the present invention provides a human antibody fragment, named CAT-212, which was derived from a scFv phage display library. CAT-212 potently neutralises human eotaxin, with an $IC_{50}$ of 650 pM in a functionally relevant (chemotaxis) bio-assay. CAT-212 is of high affinity with a $K_D$ of 15 pM. In a further embodiment, wherein the CAT-212 scFv is reformatted as a human IgG4, the antibody has been named CAT-213. CAT-213 is of similar potency to CAT-212 and neutralises human eotaxin, with an $IC_{50}$ of 700 pM in the chemotaxis assay. CAT-213 also blocks mononuclear cell chemotaxis in ovalbumin sensitised mice. Both CAT-212 and CAT-213 potently block eosinophilia in an in vivo model of allergic inflammation.

Eosinophils normally account for 1B3% of the total peripheral blood leukocytes. A marked accumulation of eosinophils, a condition known as eosinophilia, can occur in many disorders such as allergic diseases, parasitic infections and cancer (Rothenburg 1998). Eosinophilia is classified as having greater than 350 eosinophils per cubic millimeter of blood, and in severe cases levels may rise to over 5000 cells per cubic millimeter. As well as accumulating in the peripheral blood of the diseased individual, eosinophils may also selectively accumulate in any tissue in the body. Such eosinophilia can be harmful due to the pro-inflammatory effects of the eosinophils. In eosinophilic conditions such as asthma, there is frequently a correlation between the number of infiltrating eosinophils and severity of the disease.

Eosinophils accumulate at inflammatory sites where they can survive for prolonged periods, depending on the combination of cytokines produced in their immediate environment. Eosinophils contain many toxic inflammatory mediators that are stored in granules. Upon activation by one or more of a wide number of cytokines, eosinophils degranulate to release these toxins that include cationic proteins, such as major basic protein, eosinophil-derived neurotoxin and eosinophilic peroxidase. In addition, activated eosinophils also release chemoattractants, lipid mediators such as leukotrienes and a wide range of inflammatory cytokines. Many of these substances have significant cytotoxic effects on tissues, such as the respiratory epithelium in asthma (Rothenberg, 1998).

Chemokines are a group of homologous 8B10 kDa proteins (Luster, 1998) that are subdivided into families based on the relative positions of the conserved cysteine residues. Chemokines play an important role in mediating leukocyte extravasation from the blood into tissues as they provide the directional signals for the movement of leukocytes during normal development and homeostasis, and importantly, in inflammation. Although there are numerous chemotactic substances, such as leukotriene $B_4$, interleukins and bacterial products, that are able to recruit eosinophils to tissues, only the chemokine, eotaxin-1 has been shown to recruit eosinophils specifically.

Human eotaxin is a member of the rapidly expanding group of a or CC (Cys-Cys) subfamily of chemokines. This group of molecules is characterised by the presence of 4 conserved cysteines, the first 2 of which are adjacent and share a sequence identity between 20 and 75%. Members of this family include eotaxin-2 (Forssmann et al, 1997; White et al, 1997), eotaxin-3 (Shinkai et al, 1999), monocyte chemoattractant protein (MCP)-1, MCP-2, MCP-3, MCP-4, MCP-5 (Van Coillie et al, 1999), macrophage inflammatory protein (MIP)-1, MIP-LB, TARC, LARC, 1309 and RANTES.

Eotaxin-1 is an 8.4 kDa, 74 amino acid protein that was first detected in the bronchoalveolar lavage (BAL) fluid from allergen challenged sensitised guinea pigs (Griffiths-Johnson et al, 1993; Jose et al, 1994a). The molecule was first identified as a potent chemoattractant as it induced a substantial accumulation of eosinophils at its intradermal injection site. The guinea pig gene was the first cloned (Jose et al, 1994b, Rothenberg et al, 1995a), followed by mouse (Rothenberg et al, 1995b). The human eotaxin gene was subsequently identified (Kitaura et al 1996; Garcia-Zepeda et al 1996; Ponath et al, 1996) and the rat homologue has more recently been cloned (Williams et al, 1998). Human eotaxin has 61% identity with mouse and guinea pig eotaxin, and 62% identity with rat eotaxin. The human gene is located on chromosome 17 and comprises of three exons and two introns. The 5' flanking region of the gene contains a number of consensus regulatory elements, including binding sites for AP-1, NFB, interferon gamma response element and the glucocorticoid receptor, suggesting that gene expression is regulated by cytokines as well as by glucocorticosteroids.

Eotaxin can be produced by a variety of normal cell types including epithelial cells, fibroblasts, endothelial cells, T-lymphocytes, monocytes and macrophages (Cook et al, 1998; Ponath et al, 1996a; Li et al, 1997). Although eosinophils are the main effector cells for eotaxin, eosinophils also synthesize eotaxin themselves and store it in intracellular granules (Nakajima et al, 1998). The release of eotaxin from eosinophils may contribute to the local accumulation of eosinophils in inflammatory conditions. Eotaxin expression can be induced from the different cell types by many pro-inflammatory mediators, such as tumour necrosis factor-alpha, interferon and interleukin-1.

Eotaxin-2 has recently been cloned (Forssmann et al, 1997; White et al, 1997). It does not exhibit close sequence homology with eotaxin, as it shares only 39% amino acid identity. Like eotaxin, however, eotaxin-2 is a chemoattractant for eosinophils and basophils, albeit up to 10Bfold less potent. Eotaxin-3 has also been recently been identified (Shinkai et al, 1999) but its potency also appears to be 10Bfold less than that observed for eotaxin. Consequently, eotaxin-3 is chemotactic for eosinophils and basophils only at relatively high concentrations (Kitaura et al, 1999).

In general, there is substantial redundancy in the binding of chemokines to chemokine receptors. Typically, several different CC chemokines are able to bind a single chemokine receptor, and conversely, a single CC chemokine can bind to several different chemokine receptors. The chemokine receptor, CCR3, has many ligands including eotaxin, MCP-2, MCP-3, MCP-4, RANTES, eotaxin-2 and 3. Of these, eotaxin appears to be the most important. Many of the ligands, such as MCP-2, MCP-3 and RANTES, have a relatively low affinity for CCR3 and are therefore not particularly effective at inducing CCR3 mediated events. In contrast, eotaxin binds to the CC chemokine receptor 3 (CCR3) with relatively high affinity, Kd=0.52 nM (Ponath et al, 1996a). Furthermore, eotaxin is unusual among CC chemokines in that it only binds to CCR3 and not to any other chemokine receptor, that is, eotaxin is specific for CCR3.

Human CCR3 has been cloned (Combadiere et al, 1995; Daugherty et al, 1996) and is a 355 amino acid, 41 kDa, seven transmembrane domain protein. It contains four cysteines in its extracellular domain and eight serine/threonine residues in the cytoplasmic tail that are potential sites for G-protein mediated phosphorylation. CCR3 has no potential sites for N-linked glycosylation. The human receptor binds both mouse and human eotaxin with equal affinity (Daugherty et al, 1996). Mouse (Gao et al, 1996) and guinea pig (Sabroe et al, 1998) CCR3 have subsequently been cloned and share 69 and 67% amino acid identity with human CCR-3, respectively.

Human CCR-3 is principally expressed on eosinophils (Ponath et al, 1996b) and basophils (Uguccioni et al 1997; Yamada et al 1997). It is also found on $T_H2$-type T cells (Sallusto et al, 1997), microglial cells in the central nervous system (He et al, 1997) and dendritic cells (Rubbert et al, 1998). Eotaxin is a chemoattractant and activator of CCR3 expressing cells. On binding CCR3 on eosinophils, eotaxin causes intracellular calcium mobilisation, initiation of intracellular actin polymerisation, upregulation of integrin expression and the induction of oxygen radical production (Tenscher et al, 1996; Elsner et al, 1996). CCR3 is expressed at particularly high levels on eosinophils with 40,000 (Daugherty et al, 1996) to 400,000 (Ponath et al, 1996b) receptors per cell. Many CCR3 ligands, such as MCP-2, MCP-3, MCP-4 and RANTES, also bind chemokine receptors other than CCR3 and can therefore mediate chemoattraction of a wide variety of cell types. In contrast, due to its high selectivity for CCR3, eotaxin is able to specifically chemoattract and activate CCR3 expressing cells such as eosinophils.

There is a growing body of evidence that blocking the effects of eotaxin may used therapeutically. There are several in vivo studies that have used either rabbit or rodent antibodies. One such study looked at the effects of an intravenously (iv) administered anti-eotaxin antibody. Gonzalo et al (1996) injected 20 µg an anti-eotaxin rabbit polyclonal antiserum iv into ovalbumin-challenged mice. Antibody administration prior to challenge reduced the eosinophilia by 56%, as measured by the number of eosinophils accumulating in bronchoalveolar lavage (BAL) fluid.

There are also a number of reports of the effects of locally administered anti-eotaxin antibodies. Humbles et al (1997) described the co-injection of guinea pig eotaxin (10 ng) with a rabbit polyclonal anti-eotaxin antiserum (10 µl) into the skin of naïve guinea pigs that had received a prior injection of $^{111}$In-labelled eosinophils. The polyclonal antibody was able to completely block local eosinophil accumulation. Similarly, Teixeira et al (1997) used a mouse model of eosinophilia, in which murine eotaxin (1-30 pmol) was co-injected with a rabbit polyclonal anti-eotaxin antiserum intradermally into the sites of 4-8 hour active cutaneous anaphylactic reactions. Dilutions of 5% and 20% of the antiserum blocked eosinophil recruitment by 45% and 95%, respectively. In addition, Sanz et al (1998) have looked at eosinophil accumulation due to endogenously generated eotaxin induced by intradermal IL-4 injection. An anti-eotaxin polyclonal antiserum gave a 54% inhibition of the late phase (24B28 hr) but not the early phase (0B4 hr) of the response to IL-4.

To further understand the role of eotaxin in the healthy and eosinophil-mediated disease state, targeted gene disruption has been used to generate mice that are deficient in eotaxin (Rothenberg et al 1997). When these mice are sensitised and challenged with ovalbumin, eosinophil numbers were reduced by 70% in BAL from lungs of eotaxin null mice compared with wild type mice (18 hrs after challenge). This demonstrates that eotaxin enhances the magnitude of the eosinophil recruitment after antigen challenge in models of asthma. Nakamura et al. (Am. J. Resp. & Crit. Care Med. (1999) 160: 1952-1956) demonstrates association of eotaxin levels with asthma and inverse relation with lung function.

Eotaxin mRNA is constitutively produced by a number of tissues, where it has been suggested to play a role in eosinophil homing (Rothenberg et al 1995). In the eotaxin null mice, no gross histological abnormalities could be detected in any organ, including those known to express eotaxin. Similarly no changes in leukocyte phenotype could be detected. However, the total eosinophil count was reduced by 3-fold in the null mice compared to the wild-type, suggesting that eotaxin also plays a role in determining the baseline number of eosinophils in the peripheral circulation (Rothenberg et al 1997).

Specific binding members according to the present invention are useful in binding to and preferably neutralising eotaxin, with therapeutic potential in various diseases and disorders in which eotaxin plays a role. Exemplary diseases and disorders are discussed further below.

Figure 1:
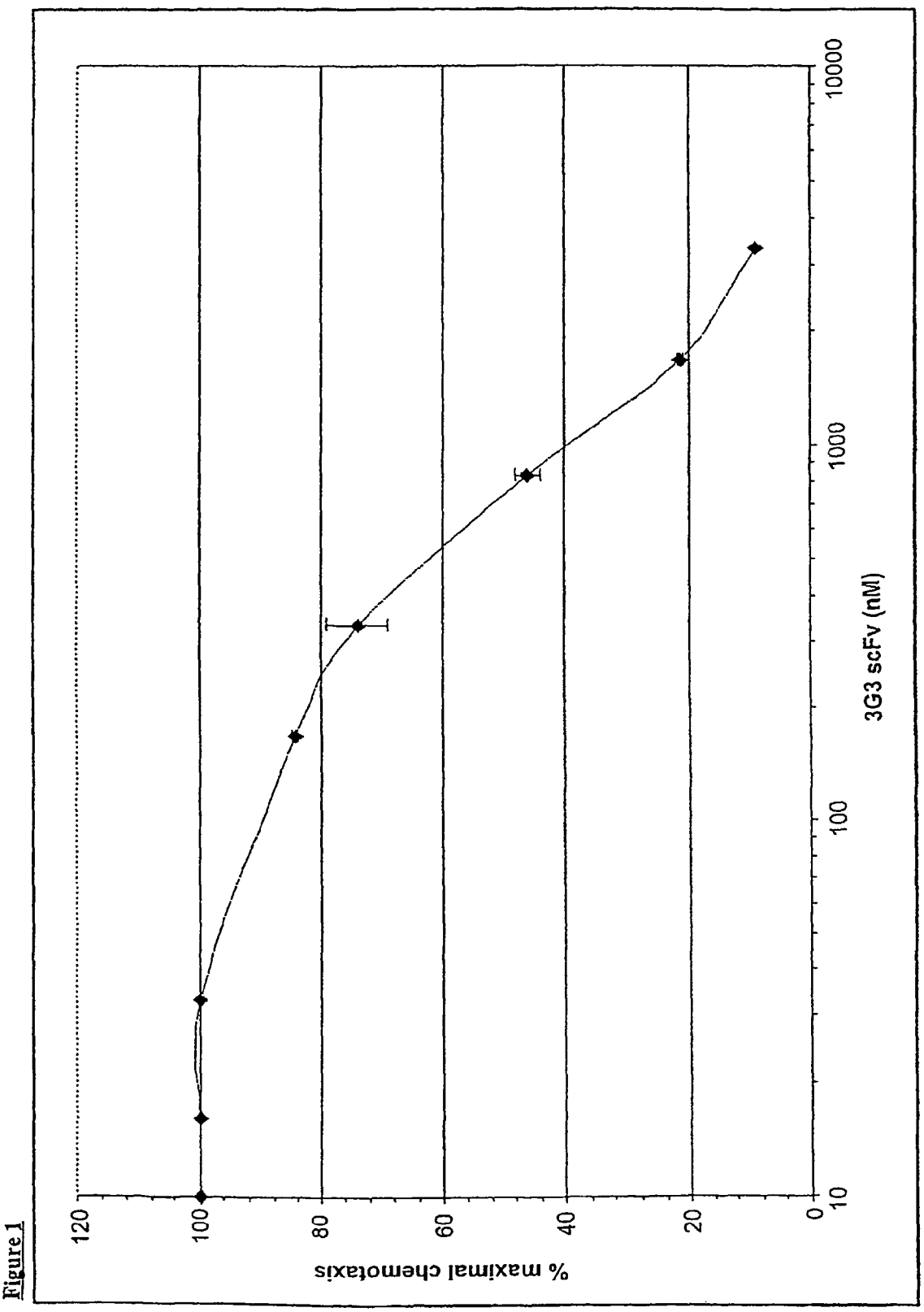
FIG. 1 shows neutralisation potency of scFv 3G3 in an eotaxin-mediated chemotaxis assay, described below. Data represent the mean with standard error bars of two separate experiments. Maximal chemotaxis is the number of cells migrating through to the lower chamber in response to 50 ng/ml human eotaxin. The $IC_{50}$ for scFv 3G3 is 800 nM.
Figure 2:
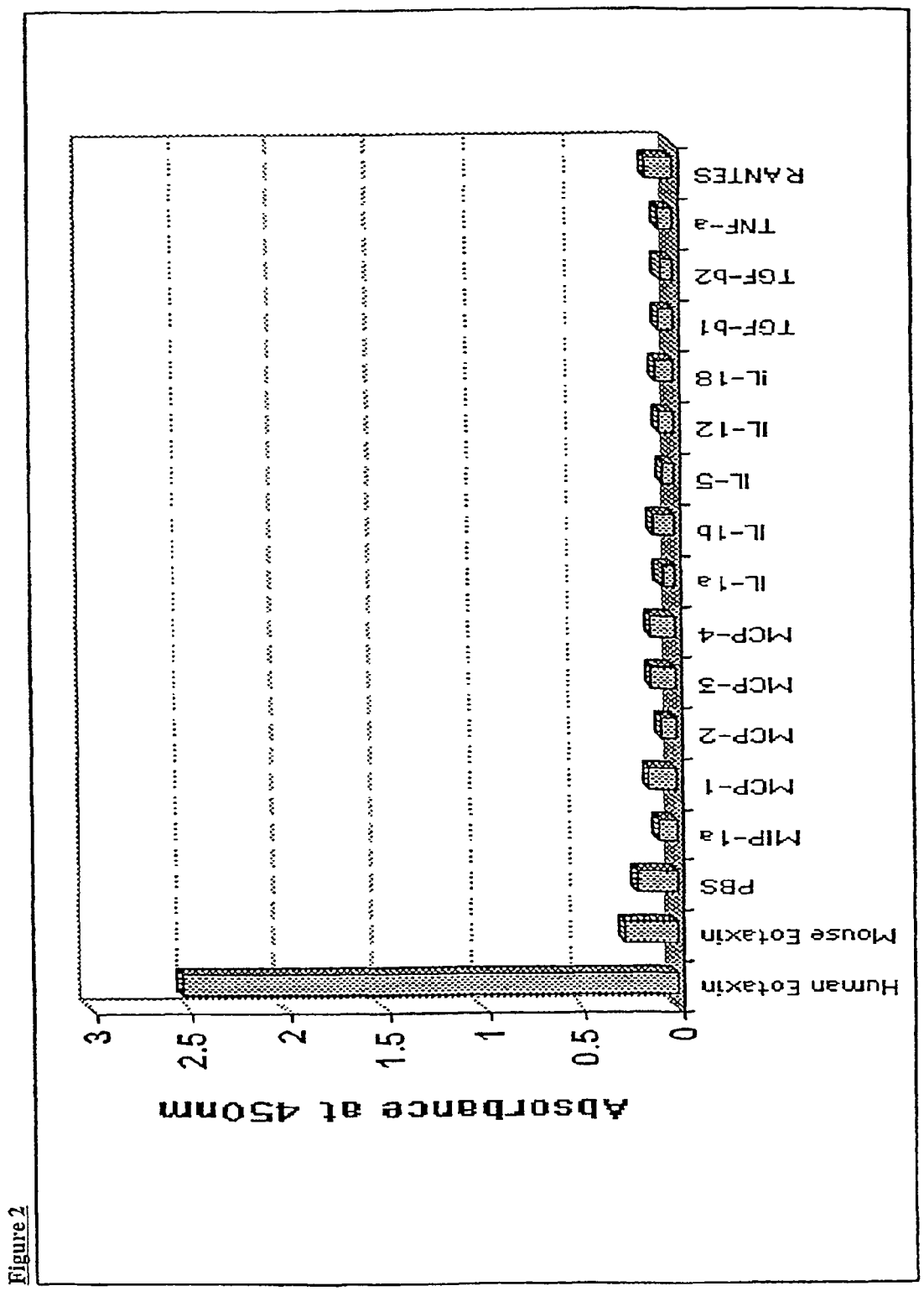
FIG. 2 shows CAT-212 specificity ELISA, with no signal above background (PBS) on any of the other related or unrelated antigens tested. A weak signal can be observed against mouse eotaxin.

In one aspect, the present invention provides a specific binding member which binds human eotaxin and which comprises the CAT-212 VH domain (SEQ ID NO. 2) and/or the CAT-212 VL domain (SEQ ID NO. 4)

Generally, a VH domain is paired with a VL domain to provide an antibody antigen binding site, although as discussed further below a VH domain alone may be used to bind antigen. In one preferred embodiment, the CAT-212 VH domain (SEQ ID NO. 2) is paired with the CAT-212 VL domain (SEQ ID NO. 4), so that an antibody antigen binding site is formed comprising both the CAT-212 VH and VL domains. In other embodiments, the CAT-212 VH is paired with a VL domain other than the CAT-212 VL. Light-chain promiscuity is well established in the art.

One or more CDRs may be taken from the CAT-212 VH or VL domain and incorporated into a suitable framework. This is discussed further below. CAT-212 VH CDR's 1, 2 and 3 are shown in SEQ ID NO.'s 5, 6 and 7, respectively. CAT-212 VL CDR's 1, 2 and 3 are shown in SEQ ID NO.'s 8, 9 and 10, respectively. Variants of the VH and VL domains and CDRs of which the sequences are set out herein and which can be employed in specific binding members for eotaxin can be obtained by means of methods of sequence alteration or mutation and screening. Such methods are also provided by the present invention.

Variable domain amino acid sequence variants of any of the VH and VL domains whose sequences are specifically disclosed herein may be employed in accordance with the present invention, as discussed. Particular variants may include one or more amino acid sequence alterations (addition, deletion, substitution and/or insertion of an amino acid residue), maybe less than about 20 alterations, less than about 15 alterations, less than about 10 alterations or less than about alterations, 4, 3, 2 or 1. Alterations may be made in one or more framework regions and/or one or more CDR's.

A specific binding member according to the invention may be one which competes for binding to antigen with any specific binding member which both binds the antigen and comprises a specific binding member, VH and/or VL domain disclosed herein, or VH CDR3 disclosed herein, or variant of any of these. Competition between binding members may be assayed easily in vitro, for example using ELISA and/or by tagging a specific reporter molecule to one binding member which can be detected in the presence of other untagged binding member(s), to enable identification of specific binding members which bind the same epitope or an overlapping epitope.

Thus, a further aspect of the present invention provides a specific binding member comprising a human antibody antigen-binding site which competes with CAT-212 or CAT-213 for binding to eotaxin.

Various methods are available in the art for obtaining antibodies against eotaxin and which may compete with CAT-212 or CAT-213 for binding to eotaxin.

In a further aspect, the present invention provides a method of obtaining one or more specific binding members able to bind the antigen, the method including bringing into contact a library of specific binding members according to the invention and said antigen, and selecting one or more specific binding members of the library able to bind said antigen.

The library may be displayed on the surface of bacteriophage particles, each particle containing nucleic acid encoding the antibody VH variable domain displayed on its surface, and optionally also a displayed VL domain if present.

Following selection of specific binding members able to bind the antigen and displayed on bacteriophage particles, nucleic acid may be taken from a bacteriophage particle displaying a said selected specific binding member. Such nucleic acid may be used in subsequent production of a specific binding member or an antibody VH variable domain (optionally an antibody VL variable domain) by expression from nucleic acid with the sequence of nucleic acid taken from a bacteriophage particle displaying a said selected specific binding member.

An antibody VH variable domain with the amino acid sequence of an antibody VH variable domain of a said selected specific binding member may be provided in isolated form, as may a specific binding member comprising such a VH domain. Ability to bind eotaxin may be further tested, also ability to compete with CAT-212 or CAT-213 for binding to eotaxin. Ability to neutralise eotaxin may be tested, as discussed further below.

A specific binding member according to the present invention may bind eotaxin with the affinity of CAT-212 or CAT-213.

A specific binding member according to the present invention may neutralise eotaxin with the potency of CAT-212 or CAT-213.

Binding affinity and neutralisation potency of different specific binding members can be compared under appropriate conditions.

In addition to antibody sequences, a specific binding member according to the present invention may comprise other amino acids, e.g. forming a peptide or polypeptide, such as a folded domain, or to impart to the molecule another functional characteristic in addition to ability to bind antigen. Specific binding members of the invention may carry a detectable label, or may be conjugated to a toxin or enzyme (e.g. via a peptidyl bond or linker).

In further aspects, the invention provides an isolated nucleic acid which comprises a sequence encoding a specific binding member, VH or VL domains according to the present invention, and methods of preparing a specific binding member, a VH domain and/or a VL domain of the invention, which comprise expressing said nucleic acid under conditions to bring about production of said specific binding member, VH domain and/or VL domain, and recovering it.

Specific binding members according to the invention may be used in a method of treatment or diagnosis of the human or animal body, such as a method of treatment (which may include prophylactic treatment) of a disease or disorder in a human patient which comprises administering to said patient an effective amount of a specific binding member of the invention. Conditions treatable in accordance with the present invention include those discussed elsewhere herein.

A further aspect of the present invention provides nucleic acid, generally isolated, encoding an antibody VH variable domain and/or VL variable domain disclosed herein.

Another aspect of the present invention provides nucleic acid, generally isolated, encoding a VH CDR or VL CDR sequence disclosed herein, especially a VH CDR selected from SEQ ID NO.'s 5, 6 and 7 or a VL CDR selected from SEQ ID NO.'s 8, 9 and 10, most preferably CAT-212 VH CDR3 (SEQ ID NO. 7).

A further aspect provides a host cell transformed with nucleic acid of the invention.

A yet further aspect provides a method of production of an antibody VH variable domain, the method including causing expression from encoding nucleic acid. Such a method may comprise culturing host cells under conditions for production of said antibody VH variable domain.

Analogous methods for production of VL variable domains and specific binding members comprising a VH and/or VL domain are provided as further aspects of the present invention.

A method of production may comprise a step of isolation and/or purification of the product.

A method of production may comprise formulating the product into a composition including at least one additional component, such as a pharmaceutically acceptable excipient.

These and other aspects of the invention are described in further detail below.

Terminology

Specific Binding Member

This describes a member of a pair of molecules which have binding specificity for one another. The members of a specific binding pair may be naturally derived or wholly or partially synthetically produced. One member of the pair of molecules has an area on its surface, or a cavity, which specifically binds to and is therefore complementary to a particular spatial and polar organisation of the other member of the pair of molecules. Thus the members of the pair have the property of binding specifically to each other. Examples of types of specific binding pairs are antigen-antibody, biotin-avidin, hormone-hormone receptor, receptor-ligand, enzyme-substrate. This application is concerned with antigen-antibody type reactions.

Antibody

This describes an immunoglobulin whether natural or partly or wholly synthetically produced. The term also covers any polypeptide or protein having a binding domain which is, or is substantially homologous to, an antibody binding domain. Examples of antibodies are the immunoglobulin isotypes and their isotypic subclasses; fragments which comprise an antigen binding domain such as Fab, scFv, Fv, dAb, Fd; and diabodies.

It is possible to take monoclonal and other antibodies and use techniques of recombinant DNA technology to produce other antibodies or chimeric molecules which retain the specificity of the original antibody. Such techniques may involve introducing DNA encoding the immunoglobulin variable region, or the complementarity determining regions (CDRs), of an antibody to the constant regions, or constant regions plus framework regions, of a different immunoglobulin. See, for instance, EP-A-184187, GB 2188638A or EP-A-239400. A hybridoma or other cell producing an antibody may be subject to genetic mutation or other changes, which may or may not alter the binding specificity of antibodies produced.

As antibodies can be modified in a number of ways, the term "antibody" should be construed as covering any specific binding member or substance having a binding domain with the required specificity. Thus, this term covers antibody fragments, derivatives, functional equivalents and homologues of antibodies, including any polypeptide comprising an immunoglobulin binding domain, whether natural or wholly or partially synthetic. Chimeric molecules comprising an immunoglobulin binding domain, or equivalent, fused to another polypeptide are therefore included. Cloning and expression of chimeric antibodies are described in EP-A-0120694 and EP-A-0125023.

It has been shown that fragments of a whole antibody can perform the function of binding antigens. Examples of binding fragments are (i) the Fab fragment consisting of VL, VH, CL and CH1 domains; (ii) the Fd fragment consisting of the VH and CH1 domains; (iii) the Fv fragment consisting of the VL and VH domains of a single antibody; (iv) the dAb fragment (Ward, E. S. et al., Nature 341, 544-546 (1989)) which consists of a VH domain; (v) isolated CDR regions; (vi) F(ab')2 fragments, a bivalent fragment comprising two linked Fab fragments (vii) single chain Fv molecules (scFv), wherein a VH domain and a VL domain are linked by a peptide linker which allows the two domains to associate to form an antigen binding site (Bird et al, Science, 242, 423-426, 1988; Huston et al, PNAS USA, 85, 5879-5883, 1988); (viii) bispecific single chain Fv dimers (PCT/US92/09965) and (ix) "diabodies", multivalent or multispecific fragments constructed by gene fusion (WO94/13804; P. Holliger et al, Proc. Natl. Acad. Sci. USA 90 6444-6448, 1993). Fv, scFv or diabody molecules may be stabilised by the incorporation of disulphide bridges linking the VH and VL domains (Y. Reiter et al, Nature Biotech, 14, 1239-1245, 1996). Minibodies comprising a scFv joined to a CH3 domain may also be made (S. Hu et al, Cancer Res., 56, 3055-3061, 1996).

Diabodies are multimers of polypeptides, each polypeptide comprising a first domain comprising a binding region of an immunoglobulin light chain and a second domain comprising a binding region of an immunoglobulin heavy chain, the two domains being linked (e.g. by a peptide linker) but unable to associate with each other to form an antigen binding site: antigen binding sites are formed by the association of the first domain of one polypeptide within the multimer with the second domain of another polypeptide within the multimer (WO94/13804).

Where bispecific antibodies are to be used, these may be conventional bispecific antibodies, which can be manufactured in a variety of ways (Holliger, P. and Winter G. Current Opinion Biotechnol. 4, 446-449 (1993)), e.g. prepared chemically or from hybrid hybridomas, or may be any of the bispecific antibody fragments mentioned above. Diabodies and scFv can be constructed without an Fc region, using only variable domains, potentially reducing the effects of anti-idiotypic reaction.

Bispecific diabodies, as opposed to bispecific whole antibodies, may also be particularly useful because they can be readily constructed and expressed in *E. coli*. Diabodies (and many other polypeptides such as antibody fragments) of appropriate binding specificities can be readily selected using phage display (WO94/13804) from libraries. If one arm of the diabody is to be kept constant, for instance, with a specificity directed against antigen X, then a library can be made where the other arm is varied and an antibody of appropriate specificity selected. Bispecific whole antibodies may be made by knobs-into-holes engineering (J. B. B. Ridgeway et al, Protein Eng., 9, 616-621, 1996).

Antigen Binding Domain

This describes the part of an antibody which comprises the area which specifically binds to and is complementary to part or all of an antigen. Where an antigen is large, an antibody may only bind to a particular part of the antigen, which part is termed an epitope. An antigen binding domain may be provided by one or more antibody variable domains (e.g. a so-called Fd antibody fragment consisting of a VH domain). Preferably, an antigen binding domain comprises an antibody light chain variable region (VL) and an antibody heavy chain variable region (VH).

Specific

This may be used to refer to the situation in which one member of a specific binding pair will not show any significant binding to molecules other than its specific binding partner(s). The term is also applicable where e.g. an antigen binding domain is specific for a particular epitope which is carried by a number of antigens, in which case the specific binding member carrying the antigen binding domain will be able to bind to the various antigens carrying the epitope.

Comprise

This is generally used in the sense of include, that is to say permitting the presence of one or more features or components.

Isolated

This refers to the state in which specific binding members of the invention, or nucleic acid encoding such binding members, will be in accordance with the present invention. Members and nucleic acid will be free or substantially free of material with which they are naturally associated such as other polypeptides or nucleic acids with which they are found in their natural environment, or the environment in which they are prepared (e.g. cell culture) when such preparation is by recombinant DNA technology practised in vitro or in vivo. Members and nucleic acid may be formulated with diluents or adjuvants and still for practical purposes be isolated—for example the members will normally be mixed with gelatin or other carriers if used to coat microtitre plates for use in immunoassays, or will be mixed with pharmaceutically acceptable carriers or diluents when used in diagnosis or therapy. Specific binding members may be glycosylated, either naturally or by systems of heterologous eukaryotic cells (e.g. CHO or NS0 (ECACC 85110503) cells, or they may be (for example if produced by expression in a prokaryotic cell) unglycosylated.

By "substantially as set out" it is meant that the relevant CDR or VH or VL domain of the invention will be either identical or highly similar to the specified regions of which the sequence is set out herein. By "highly similar" it is contemplated that from 1 to 5, preferably from 1 to 4 such as 1 to 3 or 1 or 2, or 3 or 4, substitutions may be made in the CDR and/or VH or VL domain.

The structure for carrying a CDR of the invention will generally be of an antibody heavy or light chain sequence or substantial portion thereof in which the CDR is located at a location corresponding to the CDR of naturally occurring VH and VL antibody variable domains encoded by rearranged immunoglobulin genes. The structures and locations of immunoglobulin variable domains may be determined by reference to (Kabat, E. A. et al, Sequences of Proteins of Immunological Interest. 4th Edition. US Department of Health and Human Services. 1987, and updates thereof, now available on the Internet (http://immuno.bme.nwu.edu)).

Preferably, a CDR amino acid sequence substantially as set out herein is carried as a CDR in a human variable domain or a substantial portion thereof. The VH CDR3 sequences substantially as set out herein represent preferred embodiments of the present invention and it is preferred that each of these is carried as a VH CDR3 in a human heavy chain variable domain or a substantial portion thereof.

Variable domains employed in the invention may be obtained from any germline or rearranged human variable domain, or may be a synthetic variable domain based on consensus sequences of known human variable domains. A CDR sequence of the invention (e.g. CDR3) may be introduced into a repertoire of variable domains lacking a CDR (e.g. CDR3), using recombinant DNA technology.

For example, Marks et al (*Bio/Technology*, 1992, 10:779-783) describe methods of producing repertoires of antibody variable domains in which consensus primers directed at or adjacent to the 5' end of the variable domain area are used in conjunction with consensus primers to the third framework region of human. VH genes to provide a repertoire of VH variable domains lacking a CDR3. Marks et al further describe how this repertoire may be combined with a CDR3 of a particular antibody. Using analogous techniques, the CDR3-derived sequences of the present invention may be shuffled with repertoires of VH or VL domains lacking a CDR3, and the shuffled complete VH or VL domains combined with a cognate VL or VH domain to provide specific binding members of the invention. The repertoire may then be displayed in a suitable host system such as the phage display system of WO92/01047 so that suitable specific binding members may be selected. A repertoire may consist of from anything from $10^4$ individual members upwards, for example from $10^6$ to $10^8$ or $10^{10}$ members.

Analogous shuffling or combinatorial techniques are also disclosed by Stemmer (*Nature,* 1994, 370:389-391), who describes the technique in relation to a β-lactamase gene but observes that the approach may be used for the generation of antibodies.

A further alternative is to generate novel VH or VL regions carrying a CDR-derived sequences of the invention using random mutagenesis of one or more selected VH and/or VL genes to generate mutations within the entire variable domain. Such a technique is described by Gram et al (1992, *Proc. Natl. Acad. Sci., USA,* 89:3576-3580), who used error-prone PCR.

Another method which may be used is to direct mutagenesis to CDR regions of VH or VL genes. Such techniques are disclosed by Barbas et al, (1994, *Proc. Natl. Acad. Sci., USA,* 91:3809-3813) and Schier et al (1996, *J. Mol. Biol.* 263:551-567).

All the above described techniques are known as such in the art and in themselves do not form part of the present invention. The skilled person will be able to use such techniques to provide specific binding members of the invention using routine methodology in the art.

A further aspect of the invention provides a method for obtaining an antibody antigen binding domain specific for eotaxin antigen, the method comprising providing by way of addition, deletion, substitution or insertion of one or more amino acids in the amino acid sequence of a VH domain set out herein a VH domain which is an amino acid sequence variant of the VH domain, optionally combining the VH domain thus provided with one or more VL domains, and testing the VH domain or VH/VL combination or combinations for to identify a specific binding member or an antibody antigen binding domain specific for a eotaxin antigen and optionally with one or more of preferred properties, preferably ability to neutralise eotaxin activity. Said VL domain may have an amino acid sequence which is substantially as set out herein.

An analogous method may be employed in which one or more sequence variants of a VL domain disclosed herein are combined with one or more VH domains.

A further aspect of the invention provides a method of preparing a specific binding member specific for eotaxin antigen, which method comprises:
  (a) providing a starting repertoire of nucleic acids encoding a VH domain which either include a CDR3 to be replaced or lack a CDR3 encoding region;
  (b) combining said repertoire with a donor nucleic acid encoding an amino acid sequence substantially as set out herein for a VH CDR3 such that said donor nucleic acid is inserted into the CDR3 region in the repertoire, so as to provide a product repertoire of nucleic acids encoding a VH domain;
  (c) expressing the nucleic acids of said product repertoire;
  (d) selecting a specific binding member specific for a eotaxin antigen; and
  (e) recovering said specific binding member or nucleic acid encoding it.

Again, an analogous method may be employed in which a VL CDR3 of the invention is combined with a repertoire of nucleic acids encoding a VL domain which either include a CDR3 to be replaced or lack a CDR3 encoding region.

Similarly, one or more, or all three CDRs may be grafted into a repertoire of VH or VL domains which are then screened for a specific binding member or specific binding members specific for eotaxin antigen.

A substantial portion of an immunoglobulin variable domain will comprise at least the three CDR regions, together with their intervening framework regions. Preferably, the portion will also include at least about 50% of either or both of the first and fourth framework regions, the 50% being the C-terminal 50% of the first framework region and the N-terminal 50% of the fourth framework region. Additional residues at the N-terminal or C-terminal end of the substantial part of the variable domain may be those not normally associated with naturally occurring variable domain regions. For example, construction of specific binding members of the present invention made by recombinant DNA techniques may result in the introduction of NB or C-terminal residues encoded by linkers introduced to facilitate cloning or other manipulation steps. Other manipulation steps include the introduction of linkers to join variable domains of the invention to further protein sequences including immunoglobulin heavy chains, other variable domains (for example in the production of diabodies) or protein labels as discussed in more details below.

Although in a preferred aspect of the invention specific binding members comprising a pair of VH and VL domains are preferred, single binding domains based on either VH or VL domain sequences form further aspects of the invention. It is known that single immunoglobulin domains, especially VH domains, are capable of binding target antigens in a specific manner.

In the case of either of the single chain specific binding domains, these domains may be used to screen for complementary domains capable of forming a two-domain specific binding member able to bind eotaxin.

This may be achieved by phage display screening methods using the so-called hierarchical dual combinatorial approach as disclosed in WO92/01047 in which an individual colony containing either an H or L chain clone is used to infect a complete library of clones encoding the other chain (L or H) and the resulting two-chain specific binding member is selected in accordance with phage display techniques such as those described in that reference. This technique is also disclosed in Marks et al, ibid.

Specific binding members of the present invention may further comprise antibody constant regions or parts thereof. For example, a VL domain may be attached at its C-terminal end to antibody light chain constant domains including human Cκ or Cλ chains, preferably Cλ chains. Similarly, a specific binding member based on a VH domain may be attached at its C-terminal end to all or part of an immunoglobulin heavy chain derived from any antibody isotype, e.g. IgG, IgA, IgE and IgM and any of the isotype sub-classes, particularly IgG1 and IgG4. IgG4 is preferred.

Specific binding members of the invention may be labelled with a detectable or functional label. Detectable labels include radiolabels such as $^{131}$I or $^{99}$Tc, which may be attached to antibodies of the invention using conventional chemistry known in the art of antibody imaging. Labels also include enzyme labels such as horseradish peroxidase. Labels further include chemical moieties such as biotin which may be detected via binding to a specific cognate detectable moiety, e.g. labelled avidin.

Specific binding members of the present invention are designed to be used in methods of diagnosis or treatment in human or animal subjects, preferably human.

Accordingly, further aspects of the invention provide methods of treatment comprising administration of a specific binding member as provided, pharmaceutical compositions comprising such a specific binding member, and use of such a specific binding member in the manufacture of a medicament for administration, for example in a method of making a medicament or pharmaceutical composition comprising formulating the specific binding member with a pharmaceutically acceptable excipient.

Clinical indications in which an anti-eotaxin antibody may be used to provide therapeutic benefit include asthma, eczema (atopic dermatitis) and other atopic diseases such as rhinitis, conjunctivitis, food allergy, allergic colitis which are recognised as eosinophil-mediated diseases. Experimental evidence favours eosinophils as a cause of most cases of atopy so anti-eotaxin treatment is likely to be effective for all these diseases. There are other allergic conditions, such as allergic bronchopulmonary aspergillosis and tropical eosinophilia, that feature high peripheral eosinophil counts and which may be subject to anti-eotaxin treatment.

In particular, anti-eotaxin treatment in accordance with the present invention may be used to provide clear benefit for many patients with asthma (Mattoli et al, 1997; Ying et al, 1997; Brown et al, 1998). About 10% of the population of the United Kingdom has asthma and current treatment is not entirely satisfactory: about 2000 deaths a year in England and Wales are attributed to asthma and about 6% of people with asthma are admitted to hospital (with asthmatic symptoms) each year. There is a clear need for improved treatment both for preventing asthma symptoms and to treat more severe symptoms once they have developed. Anti-eotaxin treatment may be given orally, by injection (for example, subcutaneously or in emergencies, intravenously), by inhalation (to optimise the profile of beneficial effects compared with any unwanted effects) or by alternative routes of administration. The route of administration may be determined by the physicochemical characteristics of the treatment, by special considerations for the disease, to optimise efficacy or to minimise side-effects.

Skin conditions may best be treated with topical treatment with anti-eotaxin. Diseased skin often has increased absorptive capacity, compared with healthy skin, so topical treatment may well provide the best route for therapy, where it is needed, without unwanted effects elsewhere in the body. If the skin condition covers much of the body, or if the disease is severe (maybe affecting other organs as well as the skin) then administration by injection or by other efficient means may be more appropriate that the topical route. Local injection may be appropriate under certain circumstances (see the previous paragraph).

It is envisaged that anti-eotaxin treatment will not be restricted to use in the clinic. Patients may self-administer the treatment and daily administration may be preferred over complex dosing schedules.

Combination treatments may be used to provide significant synergistic effects, particularly the combination of an anti-eotaxin specific binding member with one or more anti-interleukin-5 (IL-5) drugs. A specific binding member according to the present invention may be provided in combination or addition to one or more corticosteroids, particularly one or more systemic corticosteroids. Combination treatment with one or more other anti-asthma/anti-allergy agents, especially other Apreventers@ such as cromoglycate, leukotriene (receptor) antagonists, xanthines and long-acting bronchodilators may be employed for asthma treatment. Similar considerations of combinations apply to the use of anti-eotaxin treatment for skin and other atopic conditions.

All forms of psoriasis, urticaria (including acute urticaria, chronic recurrent urticaria, delayed pressure urticaria, cold urticaria, dermographic urticaria), prurigo nodularis, papular erythematous eruptions, pemphigoid, porphyria cutanea tarda, persistent light reaction, Wells' syndrome, eosinophilic cellulitis, drug eruptions, vasculitis (skin manifestation), purpura and other skin conditions may be treated with anti-eotaxin in accordance with the present invention. These conditions can cover a large proportion of the body, may involve organs other than the skin or may not cause the skin to have increased permeability. Even if effective applied topically, at the site of action, the preferred route may be systemic (through the body) for the same considerations as suggested for atopic indications. Severe skin disease with associated systemic manifestations is a good example of a situation in which systemic treatment may be preferred to topical treatment or local injection.

Inflammatory bowel disease (ulcerative colitis and Crohn's disease) and eosinophilic colitis/enteritis/gastroenteritis/Shulman's syndrome may be treated effectively with an anti-eotaxin therapy. Eosinophils appear as a prominent cell-type in the lesions that characterise these diseases.

Vasculitis of several forms, especially idiopathic, Hugues-Stovin syndrome, Churg-Strauss syndrome, bronchocentric granulomatosis, eosinophilic pneumonitis (Löffler's syndrome), prolonged pulmonary eosinophilia, Omenn's syndrome, Wiskott-Aldrich syndrome, familial eosinophilia and idiopathic hypereosinophilia may be treated with anti-eotaxin.

Eosinophilia of unknown cause can result complications such as pneumonitis, vasculitis, colitis, enteritis, gastroenteritis, Löffler's endocarditis and heart valve fibrosis and many syndromes affecting connective tissue. Eosinophilia can also be associated with malignant disease (especially lymphomas, leukaemias and gastrointestinal cancers), drug treatments (eg cytokine infusions) and chronic fatigue syndrome. Anti-eotaxin treatment may be employed in any of these diseases. Similarly, eosinophilia-myalgia syndrome, toxic-oil syndrome, diffuse fasciitis with eosinophilia (eosinophilic fasciitis) and eosinophilic myositis may be treated with anti-eotaxin.

The eosinophil attraction caused by parasites may be a harmful effect so intervention with anti-eotaxin in these conditions may provide benefit. The diseases involving eosinophil attraction by pathogens include protozoal infection, and metazoan infections such as helmith infestation and especially nematode infections (eg filariasis, hookworm, onchocerciasis, toxocariasis, ascariasis and trichinosis, angiostrongyliasis [eosinophilic meningitis]). Asymptomatic parasitic disease may be the cause of many of the idiopathic forms of eosinophil-mediated disease.

Anti-eotaxin treatment may have an effect on cells other than eosinophils, e.g. those expressing CCR-3 such as basophils.

In accordance with the present invention, compositions provided may be administered to individuals. Administration is preferably in a "therapeutically effective amount", this being sufficient to show benefit to a patient. Such benefit may be at least amelioration of at least one symptom. The actual amount administered, and rate and time-course of administration, will depend on the nature and severity of what is being treated. Prescription of treatment, eg decisions on dosage etc, is within the responsibility of general practitioners and other medical doctors. Appropriate doses of antibody are well known in the art; see Ledermann J. A. et al. (1991) Int J. Cancer 47: 659-664; Bagshawe K. D. et al. (1991) Antibody, Immunoconjugates and Radiopharmaceuticals 4: 915-922.

The precise dose will depend upon a number of factors, including whether the antibody is for diagnosis or for treatment, the size and location of the area to be treated, the precise nature of the antibody (e.g. whole antibody, fragment or diabody), and the nature of any detectable label or other molecule attached to the antibody. A typical antibody dose will be in the range 0.5 mg to 100 g for systemic applications, and long to 1 mg for local applications. Typically, the antibody will be a whole antibody, preferably the IgG4 isotype. This is a dose for a single treatment of an adult patient, which may be proportionally adjusted for children and infants, and also adjusted for other antibody formats in proportion to molecular weight. Treatments may be repeated at daily, twice-weekly, weekly or monthly intervals, at the discretion of the physician.

Specific binding members of the present invention will usually be administered in the form of a pharmaceutical composition, which may comprise at least one component in addition to the specific binding member.

Thus pharmaceutical compositions according to the present invention, and for use in accordance with the present invention, may comprise, in addition to active ingredient, a pharmaceutically acceptable excipient, carrier, buffer, stabiliser or other materials well known to those skilled in the art. Such materials should be non-toxic and should not interfere with the efficacy of the active ingredient. The precise nature of the carrier or other material will depend on the route of administration, which may be oral, or by injection, e.g. intravenous.

Pharmaceutical compositions for oral administration may be in tablet, capsule, powder or liquid form. A tablet may comprise a solid carrier such as gelatin or an adjuvant. Liquid pharmaceutical compositions generally comprise a liquid carrier such as water, petroleum, animal or vegetable oils, mineral oil or synthetic oil. Physiological saline solution, dextrose or other saccharide solution or glycols such as ethylene glycol, propylene glycol or polyethylene glycol may be included.

For intravenous injection, or injection at the site of affliction, the active ingredient will be in the form of a parenterally acceptable aqueous solution which is pyrogen-free and has suitable pH, isotonicity and stability. Those of relevant skill in the art are well able to prepare suitable solutions using, for example, isotonic vehicles such as Sodium Chloride Injection, Ringer's Injection, Lactated Ringer's Injection. Preservatives, stabilisers, buffers, antioxidants and/or other additives may be included, as required.

A composition may be administered alone or in combination with other treatments, either simultaneously or sequentially dependent upon the condition to be treated. Other treatments may include the administration of suitable doses of pain relief drugs such as non-steroidal anti-inflammatory drugs (e.g. asprin, paracetamol, ibuprofen or ketoprofen) or opiates such as morphine, or anti-emetics.

The present invention provides a method comprising causing or allowing binding of a specific binding member as provided herein to eotaxin. As noted, such binding may take place in vivo, e.g. following administration of a specific binding member, or nucleic acid encoding a specific binding member, or it may take place in vitro, for example in ELISA, Western blotting, immunocytochemistry, immuno-precipitation or affinity chromatography.

The amount of binding of specific binding member to eotaxin may be determined. Quantitation may be related to the amount of the antigen in a test sample, which may be of diagnostic interest, which may be of diagnostic interest.

The reactivities of antibodies on a sample may be determined by any appropriate means. Radioimmunoassay (RIA) is one possibility. Radioactive labelled antigen is mixed with unlabelled antigen (the test sample) and allowed to bind to the antibody. Bound antigen is physically separated from unbound antigen and the amount of radioactive antigen bound to the antibody determined. The more antigen there is in the test sample the less radioactive antigen will bind to the antibody. A competitive binding assay may also be used with non-radioactive antigen, using antigen or an analogue linked to a reporter molecule. The reporter molecule may be a fluorochrome, phosphor or laser dye with spectrally isolated absorption or emission characteristics. Suitable fluorochromes include fluorescein, rhodamine, phycoerythrin and Texas Red. Suitable chromogenic dyes include diaminobenzidine.

Other reporters include macromolecular colloidal particles or particulate material such as latex beads that are coloured, magnetic or paramagnetic, and biologically or chemically active agents that can directly or indirectly cause detectable signals to be visually observed, electronically detected or otherwise recorded. These molecules may be enzymes which catalyse reactions that develop or change colours or cause changes in electrical properties, for example. They may be molecularly excitable, such that electronic transitions between energy states result in characteristic spectral absorptions or emissions. They may include chemical entities used in conjunction with biosensors. Biotin/avidin or biotin/streptavidin and alkaline phosphatase detection systems may be employed.

The signals generated by individual antibody-reporter conjugates may be used to derive quantifiable absolute or relative data of the relevant antibody binding in samples (normal and test).

The present invention also provides the use of a specific binding member as above for measuring antigen levels in a competition assay, that is to say a method of measuring the level of antigen in a sample by employing a specific binding member as provided by the present invention in a competition assay. This may be where the physical separation of bound from unbound antigen is not required. Linking a reporter molecule to the specific binding member so that a physical or optical change occurs on binding is one possibility. The reporter molecule may directly or indirectly generate detectable, and preferably measurable, signals. The linkage of reporter molecules may be directly or indirectly, covalently, e.g. via a peptide bond or non-covalently. Linkage via a peptide bond may be as a result of recombinant expression of a gene fusion encoding antibody and reporter molecule.

The present invention also provides for measuring levels of antigen directly, by employing a specific binding member according to the invention for example in a biosensor system.

The mode of determining binding is not a feature of the present invention and those skilled in the art are able to choose a suitable mode according to their preference and general knowledge.

The present invention further extends to a specific binding member which competes for binding to eotaxin with any specific binding member which both binds the antigen and comprises a V domain including a CDR with amino acid substantially as set out herein or a V domain with amino acid sequence substantially as set out herein. Competition between binding members may be assayed easily in vitro, for example by tagging a specific reporter molecule to one binding member which can be detected in the presence of other untagged binding member(s), to enable identification of specific binding members which bind the same epitope or an overlapping epitope. Competition may be determined for example using the ELISA as described in Example 1.

In testing for competition a peptide fragment of the antigen may be employed, especially a peptide including an epitope of interest. A peptide having the epitope sequence plus one or more amino acids at either end may be used. Such a peptide may be said to "consist essentially" of the specified sequence.

Specific binding members according to the present invention may be such that their binding for antigen is inhibited by a peptide with or including the sequence given. In testing for this, a peptide with either sequence plus one or more amino acids may be used.

Specific binding members which bind a specific peptide may be isolated for example from a phage display library by panning with the peptide(s).

The present invention further provides an isolated nucleic acid encoding a specific binding member of the present invention. Nucleic acid includes DNA and RNA. In a preferred aspect, the present invention provides a nucleic acid which codes for a CDR or VH or VL domain of the invention as defined above.

The present invention also provides constructs in the form of plasmids, vectors, transcription or expression cassettes which comprise at least one polynucleotide as above.

The present invention also provides a recombinant host cell which comprises one or more constructs as above. A nucleic acid encoding any CDR, VH or VL domain, or specific binding member as provided itself forms an aspect of the present invention, as does a method of production of the encoded product, which method comprises expression from encoding nucleic acid therefor. Expression may conveniently be achieved by culturing under appropriate conditions recombinant host cells containing the nucleic acid. Following production by expression a VH or VL domain, or specific binding member may be isolated and/or purified using any suitable technique, then used as appropriate.

Specific binding members, VH and/or VL domains, and encoding nucleic acid molecules and vectors according to the present invention may be provided isolated and/or purified, e.g. from their natural environment, in substantially pure or homogeneous form, or, in the case of nucleic acid, free or substantially free of nucleic acid or genes origin other than the sequence encoding a polypeptide with the required function. Nucleic acid according to the present invention may comprise DNA or RNA and may be wholly or partially synthetic. Reference to a nucleotide sequence as set out herein encompasses a DNA molecule with the specified sequence, and encompasses a RNA molecule with the specified sequence in which U is substituted for T, unless context requires otherwise.

Systems for cloning and expression of a polypeptide in a variety of different host cells are well known. Suitable host cells include bacteria, mammalian cells, yeast and baculovirus systems. Mammalian cell lines available in the art for expression of a heterologous polypeptide include Chinese hamster ovary cells, HeLa cells, baby hamster kidney cells, NSO mouse melanoma cells and many others. A common, preferred bacterial host is *E. coli*.

The expression of antibodies and antibody fragments in prokaryotic cells such as *E. coli* is well established in the art. For a review, see for example Plückthun, A. Bio/Technology 9: 545-551 (1991). Expression in eukaryotic cells in culture is also available to those skilled in the art as an option for production of a specific binding member, see for recent reviews, for example Ref, M. E. (1993) Curr. Opinion Biotech. 4: 573-576; Trill J. J. et al. (1995) Curr. Opinion Biotech 6: 553-560.

Suitable vectors can be chosen or constructed, containing appropriate regulatory sequences, including promoter sequences, terminator sequences, polyadenylation sequences, enhancer sequences, marker genes and other sequences as appropriate. Vectors may be plasmids, viral e.g. 'phage, or phagemid, as appropriate. For further details see, for example, *Molecular Cloning: a Laboratory Manual:* 2nd edition, Sambrook et al., 1989, Cold Spring Harbor Laboratory Press. Many known techniques and protocols for manipulation of nucleic acid, for example in preparation of nucleic acid constructs, mutagenesis, sequencing, introduction of DNA into cells and gene expression, and analysis of proteins, are described in detail in *Current Protocols in Molecular Biology*, Second Edition, Ausubel et al. eds., John Wiley & Sons, 1992. The disclosures of Sambrook et al. and Ausubel et al. are incorporated herein by reference.

Thus, a further aspect of the present invention provides a host cell containing nucleic acid as disclosed herein. A still further aspect provides a method comprising introducing such nucleic acid into a host cell. The introduction may employ any available technique. For eukaryotic cells, suitable techniques may include calcium phosphate transfection, DEAE-Dextran, electroporation, liposome-mediated transfection and transduction using retrovirus or other virus, e.g. vaccinia or, for insect cells, baculovirus. For bacterial cells, suitable techniques may include calcium chloride transformation, electroporation and transfection using bacteriophage.

The introduction may be followed by causing or allowing expression from the nucleic acid, e.g. by culturing host cells under conditions for expression of the gene.

In one embodiment, the nucleic acid of the invention is integrated into the genome (e.g. chromosome) of the host cell. Integration may be promoted by inclusion of sequences which promote recombination with the genome, in accordance with standard techniques.

The present invention also provides a method which comprises using a construct as stated above in an expression system in order to express a specific binding member or polypeptide as above.

Aspects and embodiments of the present invention will now be illustrated by way of example with reference to the following experimentation.

Abbreviations

TES: 0.2 M Tris-HCl, 0.5 mM EDTA, 0.5 M sucrose;
2TYAG: 2TY supplemented with 100 µg/ml ampicillin and 2% glucose;
2TYAK: 2TY supplemented with 100 µg/ml ampicillin and 50 µg/ml kanamycin;
TMB: 3,3',5,5'-Tetramethyl Benzidine;
ACE: 3-amino-9-ethyl-carbazole;
$IC_{50}$: 50% inhibitory concentration;
6MPBS: 6×PBS containing 18% Marvel blocking solution;
A: Absorbance;
BSA: Bovine serum albumin;
BAL: Bronchoalveolar lavage;
CCR: CC Chemokine receptor;
CC: Cys-Cys;
DMEM: Dulbecco's Modified Eagles medium;
ELISA: Enzyme linked immunosorbent assay;
Fluo-3 AM: Fluo-3 acetoxymethyl aster;
FCS: Foetal calf serum;
gs: Glutamine synthetase;
$V_H$: Heavy chain variable;
HRP: Horseradish peroxidase;
IMAC: Immobilised Metal Affinity Chromatography;
ICC: Immunocytochemistry;
Ig: Immunoglobulin;
IPTG: Isopropyl β-D-thiogalactopyranoside;
$V_L$: Light chain variable;
MCP: Monocyte Chemoattractant Protein;
MOI: Multiplicity of infection;
Hepes: N-[2-hydroxyethyl]piperazine-N'-[2-ethanesulfonic acid];
nM: Nanomolar;

NHS: N-Hydroxysuccinimide;
NS0: Non-secreting mouse myeloma 0;
OCT: Optimum cutting tissue compound;
MPBS: PBS containing 3% Marvel;
PBS: Phosphate Buffered Saline;
PBST/0.05: Phosphate Buffered Saline+0.05% (v/v) Tween 20;
PBST: Phosphate Buffered Saline+0.1% (v/v) Tween 20;
pM: Picomolar;
PAGE: Polyacrylamide Gel Electrophoresis;
PCR: Polymerase Chain Reaction;
scFv: Single chain fragment variable;
SDS: Sodium dodecyl sulphate;
SELDI: Surface-enhanced laser desorption/ionization;
TNF-α Tumour Necrosis Factor-alpha.

LIST OF EXPERIMENTAL EXAMPLES

EXAMPLE 1: Isolation of anti-human eotaxin scFvs
EXAMPLE 2: Neutralisation potency of scFv 3G3 in a chemotaxis assay
EXAMPLE 3: Derivation and sequence of CAT-212
EXAMPLE 4: Specificity of CAT-212
EXAMPLE 5: Neutralisation potency of CAT-212 in a chemotaxis assay
EXAMPLE 6: CAT-212 competition assay for eotaxin binding to CAT-212
EXAMPLE 7: Determination of CAT-212 affinity for eotaxin
EXAMPLE 8: Mouse eotaxin competition for binding to CAT-212
EXAMPLE 9: Neutralisation potency of CAT-212 in a calcium flux assay
EXAMPLE 10: Immunoreactivity of CAT-212 with human nasal polyp
EXAMPLE 11: Conversion of CAT-212 to IgG4 format (CAT-213)
EXAMPLE 12: Neutralisation potency of CAT-213 in a chemotaxis assay
EXAMPLE 13: CAT-213 competition assay for eotaxin binding to CAT-212
EXAMPLE 14: Effects of CAT-212 and CAT-213 in an in vivo model of allergic inflammation
EXAMPLE 15: Neutralisation potency of CAT-213 in an eotaxin-mediated chemotaxis assay using L1.2 CCR-3 transfected cells: rhesus monkey and mouse eotaxin
EXAMPLE 16: Neutralisation potency of CAT-213 in an eotaxin-mediated chemotaxis assay using human eosinophils
EXAMPLE 17: Neutralisation potency of CAT-213 in an eotaxin-mediated eosinophil shape change assay

EXAMPLE 1

Isolation of Anti-Human Eotaxin scFvs scFv Antibody Repertoire

A large single chain Fv human antibody library (Vaughan et al, 1996) derived from B-lymphocytes isolated from tonsil, bone marrow and peripheral blood and cloned into a phagemid vector was used for selections. This scFv repertoire is calculated to have ca. $1.3 \times 10^{10}$ individual recombinants. Antibodies from this repertoire also incorporate a C-terminal stretch of 6 histidines to enable scFv purification by immobilised metal affinity chromatography (IMAC), and a short sequence derived from c-myc to provide a generic detection system using the monoclonal anti-c-myc antibody, 9E10.

Selection of scFv

Human eotaxin (Cambridge BioSciences)) was coated at 10 µg/ml either directly onto immunotubes (Nunc; Maxisorp), or coupled to Disuccinimidyl suberate activated BSA coated onto Maxisorb microtitre plates (Nunc). For the first round of selection, $10^{12}$ titered units of library phage were used. Three rounds of selection of the scFv library were performed following standard panning protocols (Vaughan et al, 1996). Individual clones from rounds 2 and 3 of selection were rescued and screened by phage ELISA.

Rescue of Phage for ELISA

Individual colonies from rounds 2 and 3 of selection were inoculated into 96-well plates containing 100 µl 2TY medium supplemented with 100 µg/ml ampicillin and 2% glucose (2TYAG) per well. Plates were incubated at 37° C. for 4 hours, shaking. M13KO7 helper phage was added to each well to an MOI of 10 and the plates were incubated for a further 1 hour at 37° C. The plates were centrifuged in a benchtop centrifuge at 2000 rpm for 10 minutes. The supernatant was removed and cell pellets were resuspended in 100 µl 2TY supplemented with 100 µg/ml ampicillin and 50 µg/ml kanamycin (2TYAK) and incubated at 30° C. overnight, shaking. Plates were centrifuged at 2000 rpm for 10 min and the 100 µl phage-containing supernatant from each well recovered into a 96-well plate. To block the phage, 20 µl of 6×PBS containing 18% Marvel blocking solution (6 MPBS) was added to each well and incubated at room temperature for 1 hour. The phage are now ready to use in ELISA.

Phage ELISA

Flexible 96-well plates (Falcon) were coated overnight at 40° C. with 0.5 µg/ml human eotaxin in PBS, or with PBS alone as a control. After coating, the solutions were removed from the wells, and the plates were blocked for 1 hour at room temperature in PBS containing 3% Marvel (MPBS). The plates were washed 3 times with PBS and then 50 µl of pre-blocked phage was added to each well. The plates were incubated stationary at room temperature for 1 hour. The plates were washed with 3 changes of PBS containing 0.1% (v/v) Tween 20 (PBST) followed by 3 changes of PBS at room temperature.

To each well, 50 µl of an anti-gene VIII-HRP conjugate (Pharmacia) at a 1 in 5000 dilution in MPBS was added and the plates incubated at room temperature for 1 hour. Each plate was washed 3× with PBST followed by 3× with PBS. Fifty µl of 3,3',5,5'-Tetramethyl Benzidine (TMB; Sigma) substrate was then added to each well, and incubated at room temperature for 30 minutes or until colour development. The reaction was stopped by the addition of 25 µl of 0.5 M $H_2SO_4$. The signal generated was measured by reading the absorbance at 450 nm ($A_{450}$) using a microtitre plate reader (Bio-Rad 3550).

Anti-Eotaxin scFvs

It was found to be unusually difficult to isolate eotaxin-specific scFvs, with only 4 different scFv being identified by phage ELISA. When the same scFv library has been selected against other antigens, many more scFvs are typically identified. The clone identified for further characterisation was named 3G3, and this clone consistently gave signals on human eotaxin of 5-10 fold over that seen on PBS in ELISA.

EXAMPLE 2

Neutralisation Potency of scFv 3G3 in an Eotaxin-Mediated Chemotaxis Assay

Background

The neutralisation potency of the antiBeotaxin scFv 3G3 was determined using an in vitro chemotaxis assay.

The chemotaxis assay is a particularly relevant in vitro potency assay as it is the ability of eotaxin to chemoattract CCR3 expressing cells that it is desirable to inhibit in vivo. The assay works on the principle that cells expressing the CCR3 receptor will migrate towards an eotaxin gradient by chemotaxis. The method detailed here is based on that described by Ponath et al, 1996a. Briefly, eotaxin was placed in the bottom well of a Transwell plate (Costar), along with the test antibody in an appropriate buffer. Transfected cells expressing the CCR3 receptor were placed in the top chamber of the Transwell. The two chambers were separated by a polyester membrane with a pore size of 3 µM. Cells only moved through the pores in response to a CCR3 ligand, such as eotaxin. After a defined incubation period, the number of cells that had migrated through to the bottom chamber were counted, and this number is a measure of the chemotactic activity of the chemokine that was placed in the top chamber. Inhibition of this chemotactic activity can therefore be assessed in this assay.

Maintenance of CCR3 Cells

L1.2 cells were transfected with the human CCR3 receptor to generate a stable cell line expressing CCR3 on its surface. The cells were maintained in RPMI-1640 (Sigma) containing 10% heat-inactivated FCS (Biowhittaker), 2% L-glutamine (Sigma), 10 U penicillin (Sigma), 100 g/ml streptomycin (Sigma), 250 µg/ml kanamycin (Sigma) and 400 µg/ml Geneticin (Gibco). The cells were kept between $1B2 \times 10^6$/ml for use in the assay. No stimulation of the cells to up-regulate CCR3 expression was required for the chemotaxis assay. The response to 50 ng/ml eotaxin was carefully monitored, as the number of migrating cells can decline with cell passage number, presumably due to alterations in the CCR3 expression level. Typically, a 10% sample of the cells migrating through to the lower chamber were subsequently quantitated by flow cytometry. It was found that 50 ng/ml eotaxin typically induced chemotaxis of 8,000-10,000 cells (this is the 10% value; i.e. 80,000B100,000 cells migrated through to the lower chamber in total).

Chemotaxis Assay

The chemotaxis assay buffer comprises RPMI-1640 (Sigma) containing 1% endotoxin free BSA (Bayer Pentex), 100 U/ml penicillin, 100 µg/ml streptomycin. Test solutions of antibody (in duplicate) were diluted to the desired concentration in assay buffer. A typical dilution range for IMAC-purified (see next section) scFv 3G3 was 100 µg/ml to 1 µg/ml. Human eotaxin (AlbaChem) was added to a final concentration of 50 ng/ml when mixed with the appropriate test scFv. All samples were incubated for 30 minutes at room temperature. CCR3 L1.2 cells were centrifuged at 1,200 rpm in an Heraeus Sepatech 1.0 benchtop centrifuge for 5 mins, the media removed by aspiration and the cells resuspended in 25 ml of PBS. The cells were then re-centrifuged and the cell pellet resuspended in assay buffer to $10^7$ cells/ml. Test solutions (0.6 ml per well) were placed into the bottom chambers of the Transwell plates. Transwells were placed over the test solutions and 100 µl of cells ($10^6$ cells total) placed into the top chamber of each transwell. Incubation was for 4 hours at 37° C. under 5% $CO_2$. The plates were tapped gently prior to removal of the transwells, to dislodge any cells attached to the underside of the membrane. Cells migrating through to the bottom chamber were resuspended and counted using a flow cytometer. Samples were each counted for 60 seconds using a medium flow rate. The percentage inhibition of chemotaxis caused by the test antibody was then determined.

Purification of scFv

To determine the potency of 3G3 scFv in the chemotaxis assay, scFv was first prepared by IMAC. 2TYAG (5 ml) was inoculated with a single colony of 3G3 and grown overnight at 30° C., shaking. This overnight culture was then used to inoculate 500 ml of 2TY containing 100 µg/ml ampicillin and 0.1% glucose, and grown at 30° C., shaking, until an $A_{600}$ of 1.0 was attained. Isopropyl β-D-thiogalactopyranoside (IPTG) was added to 1 mM and the culture was grown for a further 3.5 hours at 30° C.

Cells were harvested by centrifugation at 5,000 rpm, and resuspended in 10 ml of TES (0.2 M Tris-HCl, 0.5 mM EDTA, 0.5 M sucrose; ice cold). A further 15 ml of a 1:5 dilution (in water) of TES was added, and the cell suspension incubated on a turning wheel at 40° C. for 30 minutes. This caused osmotic shock and yielded a periplasmic extract containing the scFv. Residual cells and debris were pelleted by centrifugation at 9,000 rpm for 20 minutes at 40° C. The supernatant was transferred to a new tube, and 50 µl of 1 M $MgCl_2$ added. Two ml of a Ni-NTA slurry (Qiagen), pre-washed with buffer (50 mM sodium phosphate, pH 8, 300 mM NaCl) together with a protease inhibitor tablet (Boehringer Mannheim) were then added to the periplasmic extract. The preparation was incubated, rotating, overnight at 40° C. The Ni-NTA was pelleted by centrifugation at 2,000 rpm for 5 minutes, and the supernatant was aspirated. The agarose beads were washed 3 times with 50 ml wash buffer, centrifuging to collect the agarose in between each wash. Ten ml of wash buffer was added after the final wash, and the slurry was loaded on to a polyprep column (BioRad). Two ml elution buffer (50 mM NaPi, pH 8, 300 mM NaCl, 250 mM imidazole) was added to the drained agarose, and the eluate was collected. IMAC purified scFv was buffer exchanged in to PBS by use of a Nap 5 column (Pharmacia) according to the manufacturer's instructions. The $A_{280}$ was read and the protein concentration determined using a molar extinction coefficient of 1 mg/ml protein=$A_{280}$ 1.4. Purified scFv was stored in 500 µl aliquots at −70° C.

Results

Typical data for purified scFv 3G3 in the chemotaxis assay is shown in FIG. 1. The $IC_{50}$ for scFv 3G3 is 800 nM. This antibody is therefore of low-moderate potency.

EXAMPLE 3

Derivation and Sequence of CAT-212

The low-moderate potency of scFv 3G3 makes this antibody a relatively unsuitable candidate for any therapeutic application.

A further scFv antibody, named CAT-212, was obtained using a variety of techniques and its DNA sequence determined.

DNA Sequencing

DNA was amplified by polymerase chain reaction (PCR) from individual colonies on 2TYAG agar plates using the vector-specific primers pUC19reverse and fdtetseq (Vaughan et al, 1996). Amplification conditions comprise 94° C. for 1 minute, 55° C. for 1 minute and 72° C. for 2 minutes, for 30 cycles, prior to a final 10 minute extension at 72° C. The PCR products were purified using a PCR Clean-up Kit (Promega) in to a final volume of 50 µl $H_2O$. Between 2 and 5 µl of each insert preparation was used as the template for sequencing using the Taq Dye-terminator cycle sequencing system (Applied Biosystems). The primers (Osbourn et al, 1996) gene3leader, PCRHLink were used to sequence the $V_H$ and PCRLLink and mycseq10 to sequence the $V_L$ of the scFv.

The nucleotide sequences of CAT-212 $V_H$ and $V_L$ are shown in SEQ ID NO.'s 1 and 3, respectively. The derived amino acid sequence of CAT-212 $V_H$ and $V_L$ are shown in SEQ ID NO.'s 2 and 4, respectively.

The individual $V_H$ and $V_L$ segments of the antibodies were aligned to the known human germline sequences in V-BASE (Tomlinson et al, 1995) and the closest germline identified. The closest germline for the heavy chain of CAT-212 was identified as DP49, a member of the $V_H3$ family. The CAT-212 $V_H$ has just 6 changes from the DP49 germline, two of these within CDR2. The closest germline for the light chain of CAT-212 was identified as $DP_k5$, a member of the $V_k1$ family. The CAT-212 $V_L$ has only 2 changes from the $DP_k5$ germline, both within CDRs. The entire sequence of CAT-212, or any derivative thereof (such as CAT-213), has a total of only 8 changes from germline, 4 of which are in CDRs. This should further minimise any possible risk of immunogenicity when these human antibodies are used to treat patients.

EXAMPLE 4

Specificity of CAT-212

Two techniques were used to investigate the specificity of CAT-212: phage ELISA and Western blotting.
Phage ELISA To determine the specificity of CAT-212, a phage ELISA was performed against human and mouse eotaxin, and a panel of related and un-related human antigens; MIP-1α, MCP-1, MCP-2, MCP-3, MCP-4, IL-1α, IL-1β, IL-5, IL-18, IL-12, RANTES, transforming growth factor (TGF)-β1, TGF-β2, TNFα and PBS.

Individual *E. coli* colonies containing CAT-212 phagemid were inoculated into 5 ml 2YTAG and incubated at 37☐C for 4 hours, shaking. M13KO7 helper phage (Pharmacia) was added to each tube to an MOI of 10 and incubated for 30 min at 37° C. for 1 hour, the first 30 minutes static and the final 30 minutes with gentle shaking. Cells were pelleted by centrifugation at 3,500 rpm for 10 minutes and the supernatant discarded. Cell pellets were resuspended in 5 ml 2TYAK and incubated at 30° C. overnight with shaking. The next day, the cells were pelleted by centrifugation at 3,500 rpm for 10 minutes. The phage-containing supernatant (5 ml) was carefully transferred to a fresh tube, 1 ml of 6 MPBS added, and incubated at room temperature for 1 hour to pre-block the phage prior to ELISA.

Figure 9:
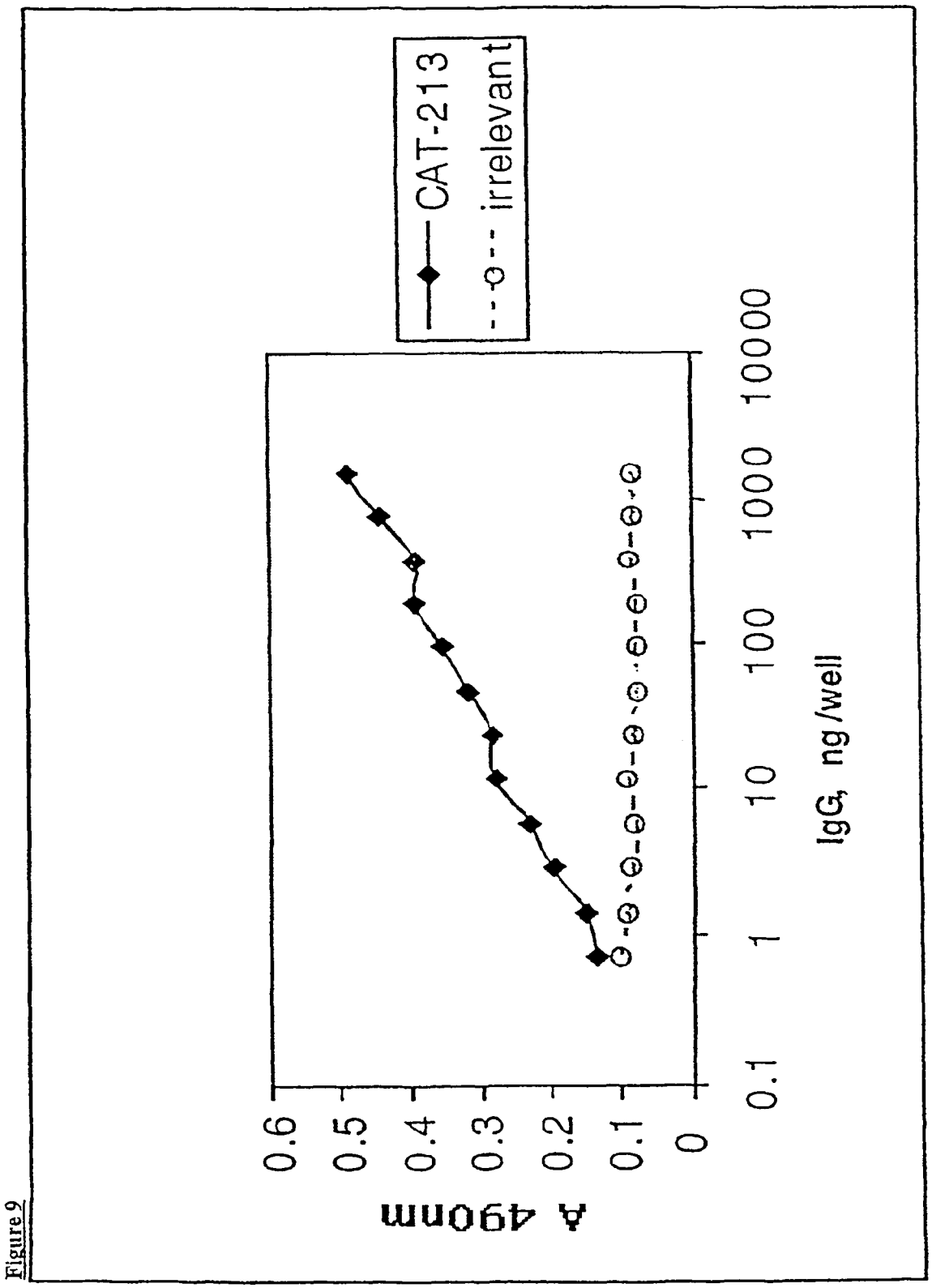
FIG. 9 demonstrates specificity of binding of CAT-213 to human eotaxin.

The coating concentrations and suppliers of the various antigens are shown in Table 1. ELISAs were performed essentially as described in Example 1. The results are shown in FIG. 9. CAT-212 is specific for human eotaxin and does not cross-react with any unrelated or related human antigen tested. A very slight signal over background was seen on mouse eotaxin. This may indicate that CAT-212 recognises mouse eotaxin, albeit relatively weakly compared to human. No commercially available eotaxin could be obtained for any species other than human or mouse.
Western Blotting Sodium dodecyl sulphate-polyacrylamide gel electrophoresis (SDS-PAGE) was performed using a PHAST system and 10B15% gels (Pharmacia). Samples of eotaxin and human MCP-1 (400 ng) were run on the gel, alongside molecular weight markers. Electrophoresis was performed then proteins were transferred to an immobilon-P (Millipore) membrane by diffusion. The membrane was blocked by incubation MPBS for 1 hour, and then probed with 10 µg/ml IMAC-purified CAT-212 scFv or an irrelevant scFv in MPBS for 1 hour, shaking at room temperature. Following this, the membrane was washed (3×2-minutes) in PBST, and then incubated with biotinylated anti-myc tag antibody (9E10) at 1 µg/ml for 1 hour. After another wash, the blot was incubated with streptavidin-HRP (Pierce) at 1 µg/ml for 1 hour, before a final wash. The blot was placed into ECL substrate (Amersham) and exposed to x-ray film (Amersham Hyperfilm ECL), following the manufacturer's instructions.

CAT-212 scFv reacted specifically with human eotaxin, as a distinct band of the predicted molecular weight was observed, while no band in the MCP-1 lane was detected. A control, irrelevant, scFv at the same concentration did not react with either eotaxin or MCP-1.

EXAMPLE 5

Neutralisation Potency of CAT-212 in an Eotaxin-Mediated Chemotaxis Assay

The potency of CAT-212 (and CAT-213, see Example 12) was tested in the chemotaxis assay, as described in Example 2. Prior to testing, monomeric scFv was prepared by FPLC gel filtration chromatography.
Preparation of Monomeric scFv Monomeric scFv was prepared by gel-filtration of IMAC-purified material on a Sephadex 75 column on a Pharmacia FPLC system. The column was run in PBS at 0.5 ml/min, and 500 µl sample was loaded. Fractions containing the purified monomeric scFv were collected. The concentration of scFv was determined by reading the $A_{280\ nm}$ of the pooled peak fractions.

Figure 3:
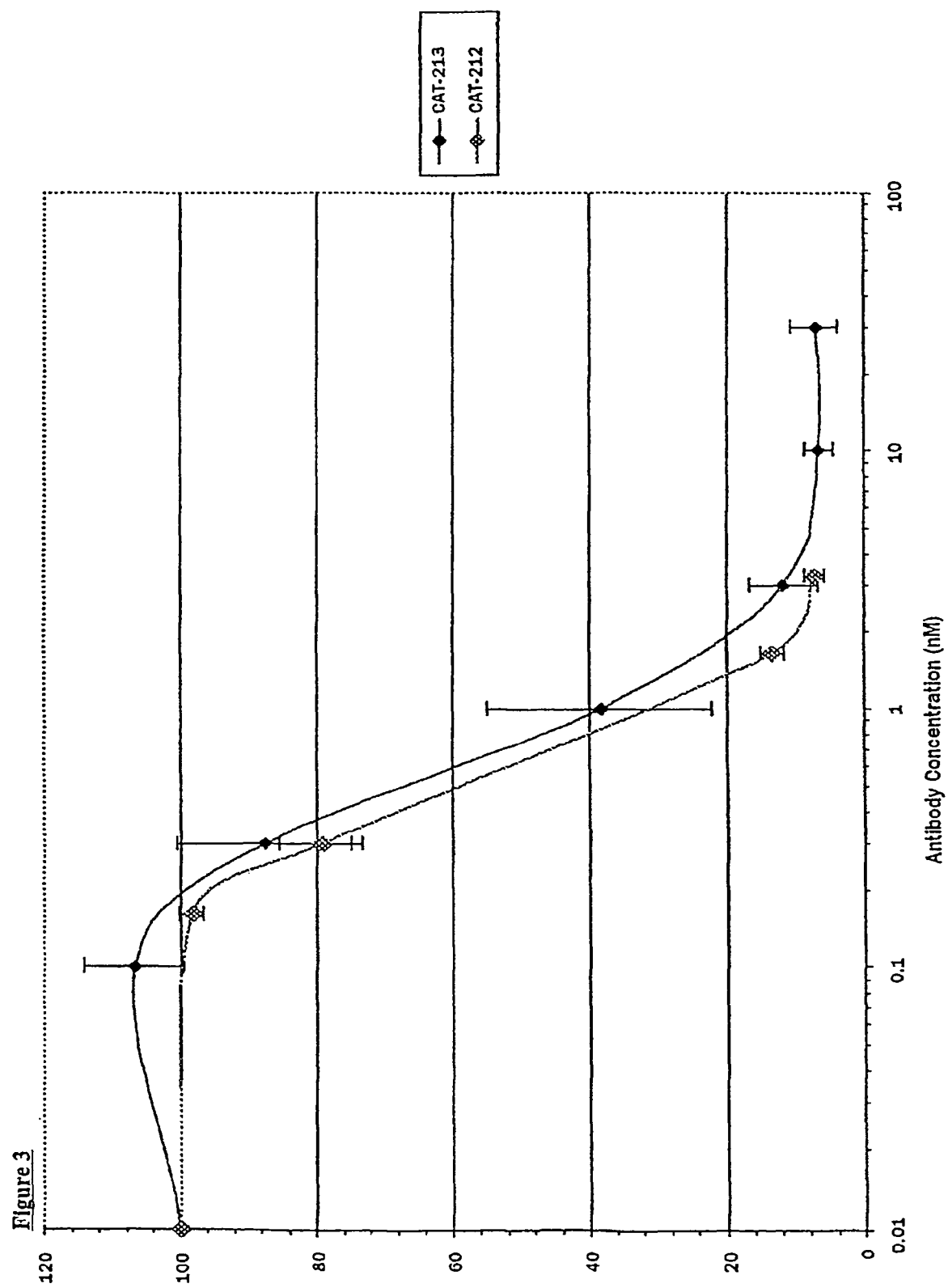
FIG. 3 shows neutralisation potency of CAT-212 and CAT-213 in an eotaxin-mediated chemotaxis assay.

A typical dilution range (in assay buffer) for CAT-212 FPLC-purified scFv was from 1 µg/ml down to 0.001 µg/ml.
Results The results are shown in FIG. 3 (mean of three estimates). CAT-212 inhibited eotaxin-mediated chemotaxis of CCR3 transfected L1.2 cells with an $IC_{50}$ of 650±83 pM. The modifications made to 3G3 had therefore led to over 1000-fold improvement in the potency of this scFv antibody. CAT-212 is a highly potent anti-eotaxin neutralising antibody.

EXAMPLE 6

CAT-212 Competition Assay for Eotaxin Binding to CAT-212 Introduction

CAT-212 when passively immobilised to a suitable polystyrene microtitre plate was shown to bind eotaxin in a concentration dependent manner as defined by its dissociation constant ($K_D$). β-emission from $^{125}$Iodine labelled eotaxin generates a detectable light signal (scintillation) when it interacts with a phosphor impregnated microtitre plate (Flash Plate™). The short range of this emission ensures that the resulting signal is due to bound antigen with little contribution from unbound material. This technique was used to determine the $K_D$ of the eotaxin-CAT-212 interaction and the relative affinity of CAT-212 and CAT-213 (see Example 13) preparations by competitive inhibition.
Assay Protocol The wells of a Flash Plate™ (NEN SMP200; 96-well) were coated with 100 µl of 40 nM IMAC-purified CAT-212 (for method of preparation, see section 2) diluted in 0.05 M carbonate-bicarbonate buffer (Sigma). The plate was sealed and incubated at 4° C. for 4 hours, then it was emptied by inversion and blocked with 150 µl 1% Marvel in PBS (Sigma) overnight at 4° C. Immediately before use the plate was emptied by inversion and washed 3 times with PBS, then blotted dry.

The assay buffer was composed of RPMI medium (Sigma) containing 0.5% bovine serum albumin (Sigma). Test samples were diluted 3-fold in buffer to give 11 concentrations in duplicate. Fifty µl of diluted test sample was added to wells, followed by 50 µl of 30 pM [$^{125}$I]eotaxin (Amersham). The plate was sealed and incubated at room temperature for 1-2 hours. The plate was counted on the Packard Topcount scintillation counter (wells counted for 2 minutes each).

Data was analysed using a 4-parameter logistic equation using GraphPad Prism (GraphPad Inc) to give apparent $IC_{50}$ values. Y=Bottom+(Top-Bottom)/(1+10^(LogIC50–X) *HillSlope)) X=logarithm of concentration, Y is the CPM.

Results

Figure 4:
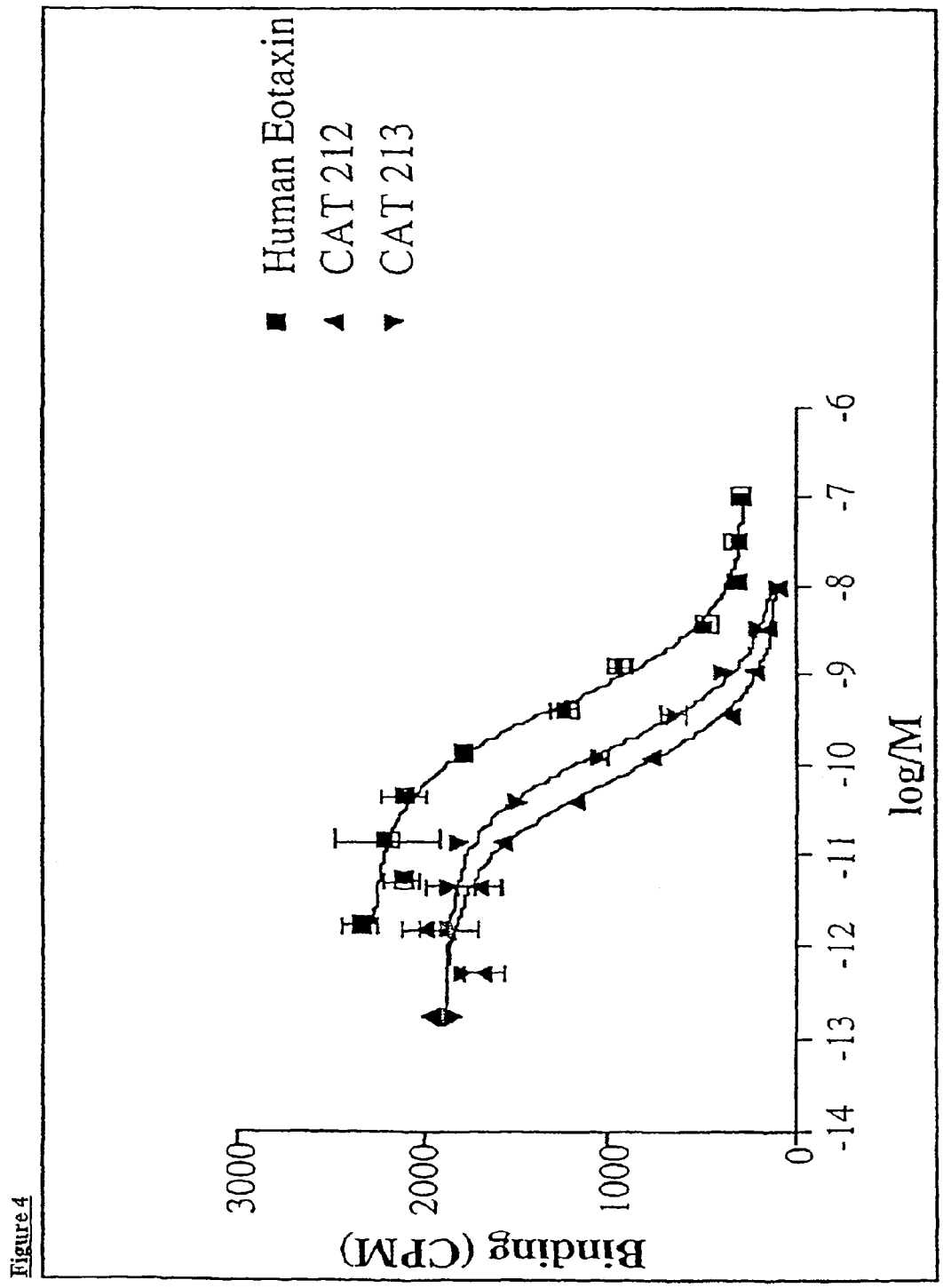
FIG. 4 illustrates $IC_{50}$ of CAT-212 and CAT-213 in a competition assay.

FIG. 4 shows the results of an assay in which unlabelled CAT-212, was used to compete for [$^{125}$I]eotaxin binding to CAT-212 coated to a flash plate. CAT-212 demonstrates an $IC_{50}$ of 42.5 pM in this assay (mean of 4 estimates).

EXAMPLE 7

Determination of CAT-212 Affinity for Eotaxin

Assay Protocol

A Flash Plate™ was coated with CAT-212 and reagents prepared as described in Example 6. A serial two fold dilution of [$^{125}$I]eotaxin +/– one hundred fold excess of unlabelled eotaxin in Assay Buffer was prepared and 100 µl samples in duplicate added to the coated plate. The samples were sealed and incubated for two hours at room temperature and counted.

The data was analysed by non-linear curve fitting using the KELL for windows software package (Biosoft) according to the formula: $Y=(B_{MAX}*[L])/(K_D+[L])$ Where [L] is the free ligand concentration, $K_D$ the affinity and $B_{MAX}$ the maximum binding site concentration.

Figure 5:
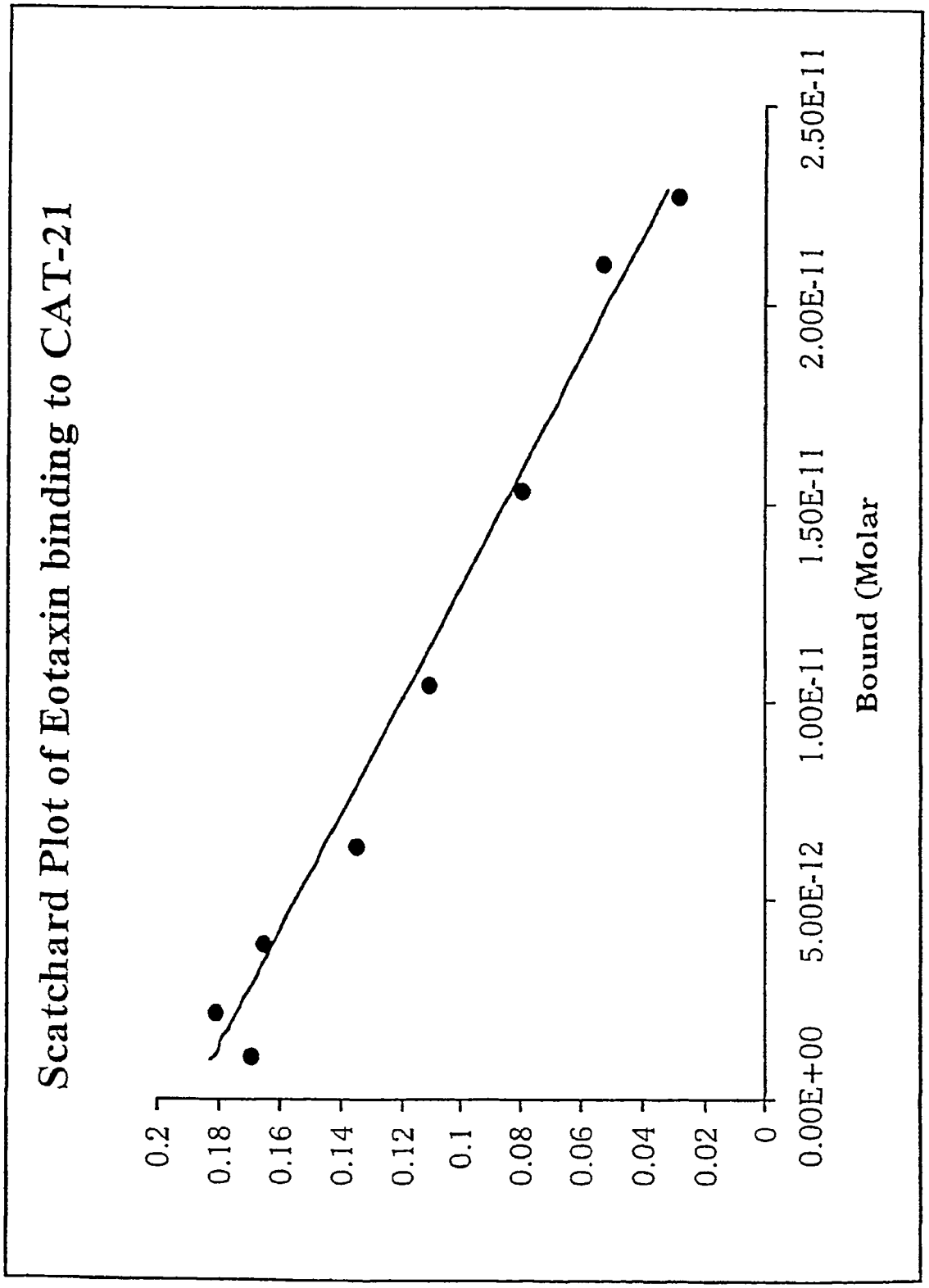
FIG. 5 shows a Scatchard plot of eotaxin binding to CAT-212, used in determination of CAT-212 affinity for eotaxin.

The data is then visualised by the use of the Scatchard Plot (FIG. 5) of the bound/free ratio vs bound giving a straight line with a slope=–1/$K_D$ and an x-intercept of $B_{MAX}$ when the ligand is binding to a homogeneous population of binding sites.

Results

From the Scatchard plot (FIG. 5), the affinity for eotaxin binding to CAT-212 was estimated at 146 pM.

EXAMPLE 8

Mouse Eotaxin Competition for Binding to CAT-212

Introduction

To address the in vivo activity of CAT-212/CAT-213, two strategies were employed (see Example 14):
(1) Effecting eosinophilia in a mouse model by injection of human eotaxin;
(2) Effecting eosinophilia in a mouse model by inducing the production of endogenous eotaxin.

For the second approach, it was first necessary to determine whether CAT-212/CAT-213 recognise mouse eotaxin.

Assay Protocol

Flash Plate™ was prepared as described in Example 6. Eleven serial one in three dilutions of unlabelled human and mouse Eotaxin (R&D) in Assay Buffer and mixed with $^{125}$I-Eotaxin prepared at an estimated concentration of 30 pM and 100 µl added to the wells in duplicate. The plate was sealed and incubated at room temperature for two hours, counted and the data processed as described in Example 6.

Results

Figure 6:
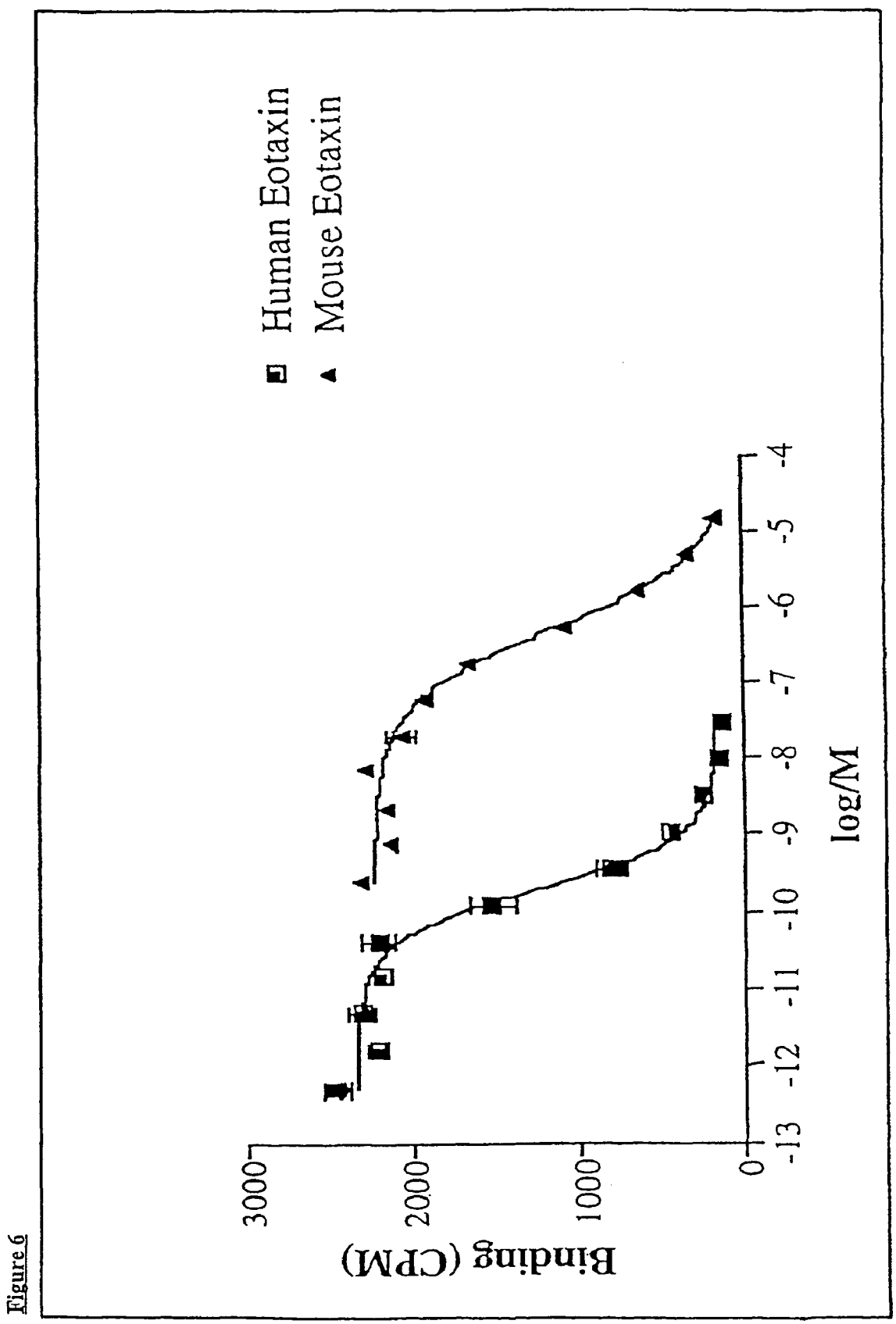
FIG. 6 illustrates mouse eotaxin competition for binding to CAT-212.

The $IC_{50}$ estimate for CAT-212 binding to mouse eotaxin is 296 nM (mean of two estimates). The data are shown in FIG. 6. CAT-212 therefore recognises mouse eotaxin.

EXAMPLE 9

Neutralisation Potency of CAT-212 in a Calcium Flux Assay

Introduction

This functional assay is designed to measure the increase in intracellular $Ca^{2+}$ produced when a receptor is bound and activated by its ligand. In this case, cells transfected with CCR3 are loaded with a $Ca^{2+}$ sensitive fluorescent dye (fluo-3AM) and fluorescence monitored over time using FLIPR. In FLIPR, measurement of fluorescence in every well is performed at programmed intervals (every 1 or 5 sec) and reagent is added simultaneously to each well. The increase in intracellular $Ca^{2+}$ concentration induced by eotaxin binding the CCR3 receptor is measured and is proportional to the increase in fluorescence. The inhibition of this response caused by CAT-212 binding to and neutralising eotaxin can be quantitated.

Assay Protocol

CCR3 cells were activated by supplementing the usual culture medium with 0.5 µg/ml sodium butyrate (Sigma) for 24 hours prior to the experiment to increase CCR3 expression and thus the magnitude of the response to eotaxin. Activated CCR3 cells were washed twice in RPMI1640 and then resuspended at 4×10$^6$ cells/ml in RPMI1640 containing freshly prepared 2 µM fluo-3AM (Molecular-Probes), 0.03% pluronic acid (Molecular Probes) and 0.1% FCS. The cells were then incubated for 45 min at 37° C. Following this, they were washed once in RPMI1640 and twice in FLIPR buffer (125 mM sodium chloride, 5 mM potassium chloride, 1 mM magnesium chloride, 1.5 mM calcium chloride, 25 mM Hepes, 5 mM glucose and 0.1% FCS, pH 7.4). They were finally resuspended in FLIPR buffer at 1×10$^6$/ml and 100 µl plated out onto a 96-well black-walled plate with a clear base (Corning) to give 1×10$^5$ cells per well. The plate was then centrifuged at 1000 rpm for 5 min to give an even, relatively dense, monolayer of cells.

A dilution series of CAT-212 was prepared at 6× final concentration (final 200 nM-1.6 nM) and pre-incubated with an equal volume of 60 nM eotaxin (Cambridge Bioscience) for 10 minutes at room temperature. All treatments were prepared in at least duplicate using FLIPR buffer in a final volume of 100 µl in a 96-well polystyrene plate (Corning). The final concentration of eotaxin on the cells was 10 nM.

The plate containing the fluo-3-loaded cells was placed in FLIPR and fluorescence readings made every 1 sec for the first 60 sec then at 5 sec intervals until the end. The experiment was performed at room temperature. For the experiment, 50 µl of each treatment was added to every well after a 10 sec interval.

Results

Figure 7:
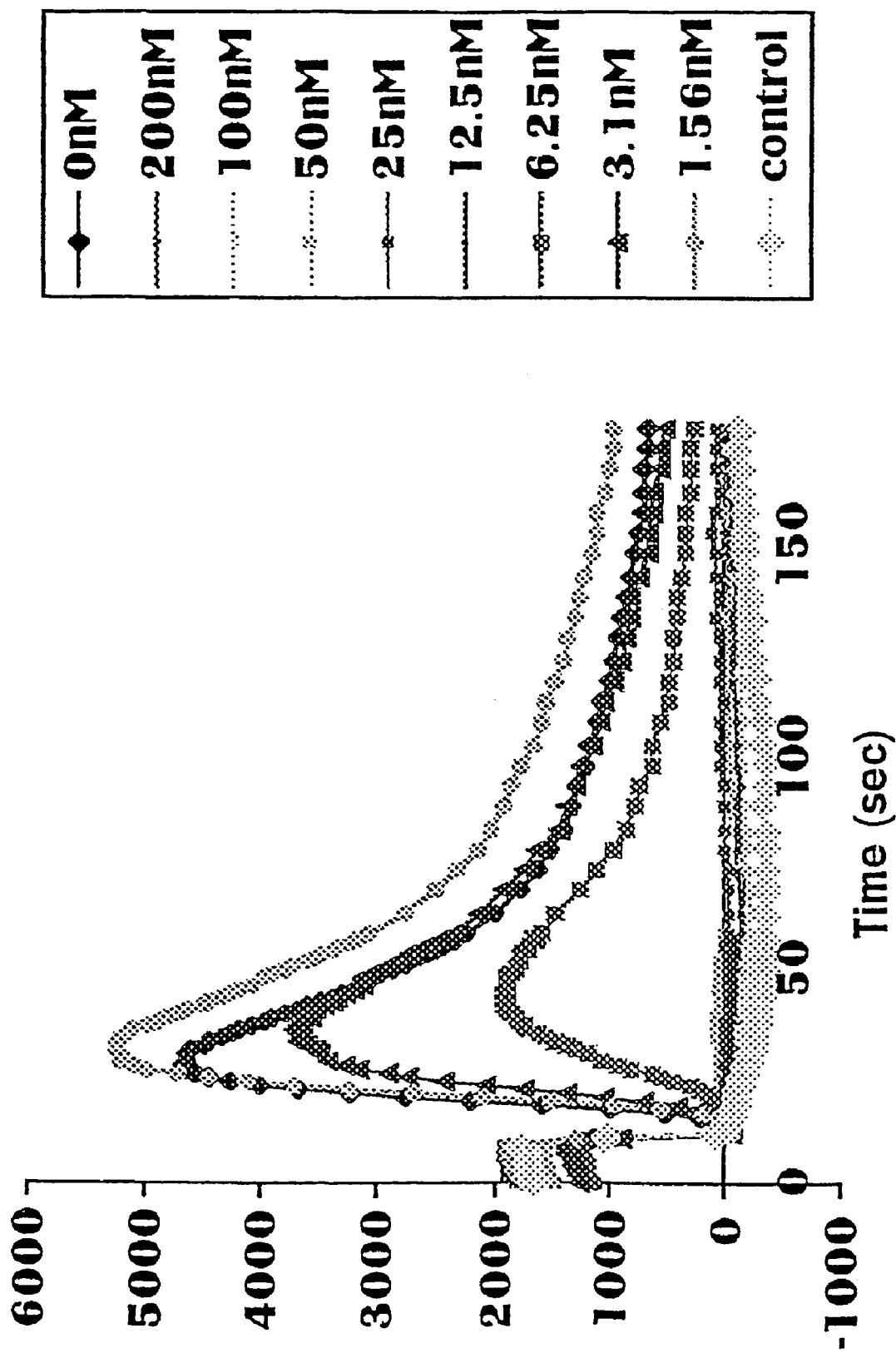
FIG. 7 shows neutralisation by CAT-212 of the increase in intracellular $Ca^{2+}$ concentration induced by eotaxin. Change in fluorescence measured over time in FLIPR in response to the addition of 10 nM eotaxin+/−CAT-212 (concentration of CAT-212 shown in legend). Control is the addition of buffer alone. Addition of the Ab alone does not change the fluorescence significantly. The average of triplicate wells for eotaxin and duplicate wells for each antibody concentration is shown.
Figure 8:
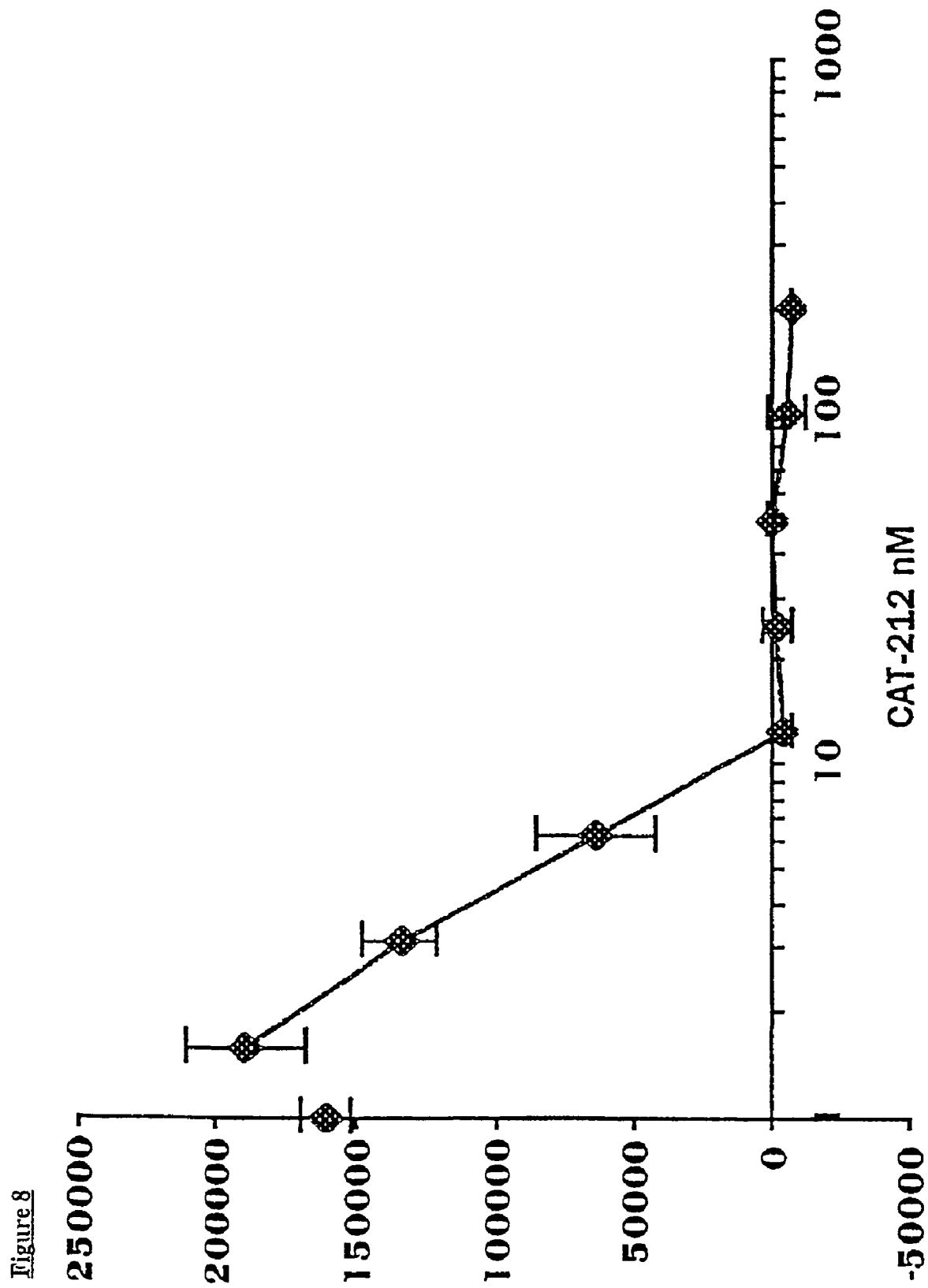
FIG. 8 shows area under the curve data for CAT-212 in a calcium flux assay, calculated for data from 12 s to 100 s. the lone point on the y-axis is eotaxin alone. Average and std dev of triplicate wells for eotaxin and duplicated wells for each antibody concentration are shown.

The results of this experiment are illustrated in FIG. 7. It can be seen that CAT-212 gives a dose dependent inhibition of $Ca^{2+}$-flux produced by eotaxin binding its receptor on CCR3 cells. FIG. 8 shows "the area under the curve" for this data giving an approximate $IC_{50}$ value of 5 nM.

EXAMPLE 10

Immunoreactivity of CAT-212 with Human Nasal Polyp

Introduction

Human nasal polyp is an inflammatory tissue characterised by an infiltration of eosinophils. Eotaxin expression has been documented as being up-regulated in nasal polyp and eotaxin protein may be detected by immunocytochemistry using anti-eotaxin antibodies (Ponath et al., 1996a). CAT-212 was therefore screened for immunoreactivity with sections of human nasal polyp.

Preparation of Tissues for ICC

Human nasal polyp tissue was obtained from surgical samples. Tissues were cut into 5 mm³ chunks and mounted onto cork pieces using a drop of optimum cutting tissue compound (OCT; Sakura). To freeze the tissues, 20 mls of isopentane was cooled in a bath of liquid nitrogen and the mounted tissues immersed for 30 seconds. The frozen tissues were then placed into a cryotube and immersed in liquid nitrogen for a further 30 seconds. Tissue blocks were stored frozen at B70° C. To cut sections, OCT compound was applied to a cryostat chuck and the frozen tissue embedded. The chuck and tissue were then snap frozen for 30 seconds in liquid nitrogen. The tissue was then mounted onto a cryostat and 5 micron cryosections of each human tissue cut onto microscope slides.

Preparation of Phage Antibodies for ICC

Phage antibody clones were rescued as described in Example 1. Phage-containing supernatant was preblocked with 1% BSA before use in ICC.

Protocol

Human tissue sections were fixed by immersion in acetone at ambient temperature for 15 minutes, air dried and then washed three times in PBSt for 10 minutes (total). The test scFvs were diluted in PBST and applied to the sections for 2 hours at room temperature. Slides were washed 3 times in PBST and incubated with mouse 9E10 antibody diluted 1/100 in PBST. Sections were washed 3 times in PBST and incubated in EnVision anti-mouse peroxidase polymer as supplied (DAKO K4006) for 30 minutes. Sections were again washed 3 times in PBST and stained with 3-amino-9-ethyl-carbazole peroxidase substrate (AEC; Sigma). AEC substrate was prepared by diluting a stock solution (2.4 mg/ml of AEC dissolved in dimethylformamide) 1:10 in 20 mM sodium acetate buffer, pH 5.2 and adding 0.15% (v/v) of hydrogen peroxide. One hundred µl of AEC substrate solution was added to each section and incubated for 5-10 minutes followed by washing in tap water containing 0.1% Tween to stop colour development. The slides were then counterstained with haematoxylin (DAKO S2020) for <5 seconds and then washed 3 times in water. Washed sections were then coated in aqueous mount and a glass cover slip applied.

Results

CAT-212 at 30 µg/ml stained sections of human nasal polyp in an equivalent manner to that seen with a positive control anti-eotaxin antibody (Cambridge Bioscience) at 50 µg/ml. There was no detectable staining in the substrate only control or with an irrelevant scFv at the same concentration. CAT-212 demonstrated specific cytoplasmic staining in the covering epithelium, and in elongated mononuclear cells and endothelium situated in the stroma of nasal polyp. This is consistent with the published ICC profile obtained with an anti-eotaxin antibody on nasal polyp (Ponath et al., 1996a). To confirm that the staining was specific for eotaxin, a competition ICC was undertaken in which 40 µg/ml CAT-212 was pre-bound to 133 µg/ml, 660 µg/ml and 1.33 mg/ml eotaxin prior to addition to the nasal polyp sections. CAT-212 alone gave good staining as described above. When CAT-212 was pre-bound to eotaxin, there was a dose-dependent inhibition of binding to nasal polyp with 1.33 mg/ml eotaxin virtually abolishing all specific staining.

EXAMPLE 11

Conversion of CAT-212 to IgG4 Format (CAT-213)

Introduction

The vectors used in the conversion of the scFv (CAT-212) into whole antibody (IgG4; CAT-213) format were as follows: pGamma4 ($V_H$ expression vector) and pMR15.1 ($V_L$ expression vector). Both of these vectors were obtained from Lonza Biologics.

Protocol

All primers used are referenced to SEQ ID NO.'s in Table 3. The $V_H$ DNA and $V_K$ DNA were initially amplified up using oligonucleotides p113/p132 and p109a/p110b respectively. All the PCR reactions used PwoI polymerase (Roche) for its proof reading capabilities and PCR conditions were 25 cycles of 94° C., 30 seconds; 50° C., 30 seconds; 72° C., 60 seconds. The signal sequence for both $V_H$ and $V_K$ were added on by amplification with p10/p132 and p11/p110b respectively. The $V_H$ and $V_K$ fragments of DNA were digested in parallel with their acceptor vectors, with HindIII, ApaI and BstBI, BsiWI respectively. Fragments were then ligated together, thus constructing the separate plasmids. Both plasmids were digested with BamHI and Not I and ligated together to form the final construct. All the restriction digests and ligations were performed using enzymes from New England Biolabs, using the buffers recommended by the supplier.

For transformation of the vectors, electrocompetent E. coli cells (DH5α) were used. The electroporation was carried out in 0.2 cm gap electroporation cuvettes, into which 5 µl of ligated DNA was added to 100 µl of E. coli cells. The cells were given a single pulse of 2.5 kV at 200Ω followed by a 20 minute recovery period in 2TY at 37° C. in a shaking incubator. Aliquots were plated out onto 2TYAG agar plates and incubated at 37° C. overnight. The following day the colonies were picked and screened by PCR using Taq polymerase and the appropriate primers.

A clone with a correctly-sized insert was grown in 100 ml 2TY (containing 100 µg/ml ampicillin) overnight at 37° C. in a shaking incubator. The cells were harvested by centrifugation at 3,000 g for 15 minutes, and a QIAGEN maxi-prep kit was used to extract the plasmid DNA. The DNA concentration was determined spectrophotometrically assuming that an $A_{260\ nm}$ of 1=50 µg/ml. The final construct was sequenced with primers p24, p34 and p36 and p37 to confirm the correct sequence.

A 36 plate transfection was performed in NS0 cells by electroporation (250V) using the gs system (Lonza) using the glutamine synthetase gene as the selectable marker. Wild type NS0 cells were grown in DMEM (Sigma) containing 10% dialysed FCS with 2 mM glutamine. $6\times10^7$ NS0 cells were transfected with 300 µg of DNA, linearised by Pvu I. After electroporation the cells were resuspended in DMEM with glutamine and plated out into 36×96-well plates (50 µl/well) and incubated at 37° C. in 5% $CO_2$. The following day, 150 µl/well of selective medium (DMEM without glutamine) was added. After approximately 3 weeks the colonies were screened by ELISA (see below) using an irrelevant antibody as a negative control. All colonies producing >20 µg/ml were expanded into 24-well plates and then into duplicate T25 flasks. One flask was grown to saturation and the other frozen down. The first cell line (not clonal) named 4B7 was adapted to serum free medium and expanded to 2 L volume for purification using protein A.

Screening ELISA Assay to Detect IgG Expression

Each well of an ELISA plate (Immulon 4, Dynex technologies) was coated with 100 µl of 1 µg/ml goat anti-human IgG (Harlan) in 50 mM sodium bicarbonate/carbonate buffer, pH 9.6, at 4° C. overnight. Plates were washed 3 times in PBS containing 0.05% (v/v) Tween 20 (PBST/0.05). CAT-213 was diluted in PBST/0.05 and a series of 2-fold dilutions were generated across the plate. The plate was incubated for 1 hour at room temperature, and then washed 3 times in PBST/0.05. One hundred 1 of 1:5000 HRP conjugated goat anti-human IgG antibody (Harlan), diluted in PBST/0.05 was added to each well and incubated for 30 minutes at room temperature. The plate was washed 3 times in PBST/0.05. Following this, 100 µl freshly prepared HRP substrate buffer (0.4 mg/ml o-phenylenediamine in 24 mM citric acid, 52 mM sodium hydrogen phosphate, pH 5.2, containing 5 1 $H_2O_2$/50 ml buffer added just before use) was added to each well. After 5-10 minutes the reactions were stopped with the addition of 50 µl 12.5% sulphuric acid. The $A_{490}$ was measured.

The cell line initially expressing the highest amount of IgG, as indicated by a high signal in the screening ELISA, was chosen for expansion. This entailed expanding it from a 96 well plate up to a T75 flask. This cell line was then adapted to a serum free medium (Lonza NM2) involving serial dilutions, decreasing the serum by half every time (starting percentage of serum is 10%). Once adapted to serum free medium, the cell line was then grown to saturation in 150 ml flasks, and harvested at less than 10% cell viability. The supernatant was clarified by centrifugation then filtered through a 0.22 µm filter. The antibody was purified from the supernatant using a Protein A affinity column.

Binding assay to detect anti-eotaxin specific IgG Each well of an ELISA plate (Immulon 4, Dynex technologies) was coated with 100 µl 0.5 µg/ml eotaxin (Albachem) in 50 mM sodium bicarbonate/carbonate buffer, pH 9.6, at 4° C. overnight. The rest of the protocol is the same for the screening assay (see section above). Results, including an irrelevant control antibody, are shown in FIG. 9.

EXAMPLE 12

Neutralisation Potency of CAT-213 in an Eotaxin-Mediated

Chemotaxis Assay
Assay Protocol

The potency of CAT-213 was tested in the chemotaxis assay, essentially as described in Example 2. Prior to testing, CAT-213 was purified from the supernatant using a Protein A affinity column (as in Example 11). A typical dilution range for Protein A purified CAT-213 was from 100 nM down to 0.03 nM in assay buffer.

Results

The results of this assay are shown in FIG. 3. CAT-213 inhibited eotaxin-mediated chemotaxis of CCR3 transfected L1.2 cells with an $IC_{50}$ of 700±350 pM. The potency is similar to that seen for CAT-212 in this assay.

EXAMPLE 13

CAT-213 Competition Assay for Eotaxin Binding to CAT-212

Assay Protocol

The Flash Plate assay was performed essentially as described in Example 6. The Flash Plate was coated with 40 nM CAT-212. CAT-212, CAT-213, and eotaxin were diluted in assay buffer and 50 l added to the wells followed by 50 l of 60 pM [$^{125}$I]eotaxin.

Results

The $IC_{50}$ of CAT-213 in this assay is 59.3 pM (mean of 4 estimates, FIG. 4). This is similar to the value obtained for the scFv, CAT-212.

EXAMPLE 14

Effects of CAT-212 and CAT-213 in an In Vivo Model of Allergic Inflammation

The air pouch model of allergic inflammation was chosen as a convenient model in which to study eosinophilia. Dexamathasone (a steroidal anti-inflammatory drug) has been shown to block eosinophil recruitment to the air pouch in this model (see Das et al., 1997). Other anti-eotaxin antibodies have previously been shown to block eosinophil recruitment in a range of in vivo models (discussed already above) in which eosinophilia was stimulated with either local administration of eotaxin or induced by ovalbumin (antigen) challenge in ovalbumin sensitized animals.

The effects of CAT-212 or CAT-213 were investigated in the air pouch model in ovalbumin sensitized mice in which eosinophilia was induced by either recombinant human eotaxin or ovalbumin administered intra-air pouch (i.po.).

Methods

Female Balb/c mice (17B21 g, supplied by Harlan U.K. or Charles River) were housed within the Small Animal Barrier Unit at Babraham Institute (Cambridgeshire) Mice was housed 3 to a cage with a 12 h day/night cycle (lights on 7 am). Animals were allowed to acclimatize to the animal house for at least 2 weeks prior to experimentation and allowed food and water ad libitum.

Sensitization was carried out as reported by Das et al., 1997. Briefly, mice were sensitized to ovalbumin by subcutaneous (s.c.) injection of 100 g ovalbumin in aluminium hydroxide gel (0.4 ml of a saline containing 3.3 mg aluminium hydroxide; Rehydragel) on days 1 and 8. An air pouch was formed on the back of the mice in the manner previously reported by Das et al., 1997. On day 9, mice were anaesthetised with isoflurane and 2.5 ml sterile air (0.25 m filtered) injected s.c. on the back of each mouse. On day 12, mice were injected with a further 2.5 ml sterile air to re-inflate the air pouch. On day 15 mice were challenged with either eotaxin or ovalbumin.

Human Eotaxin Challenge Procedure

In a pilot experiment it was established that human recombinant eotaxin (Albachem) administered i.po. could evoke eosinophilia in ovalbumin sensitized mice. 30 min before administration of human eotaxin, recombinant murine IL-5 (IL-5; 100 pmol kg$^{-1}$) was injected intravenously (i.v.) to increase the circulating pool of eosinophils (see Collins et al., 1995). After 6 h, human eotaxin (1 µg, 0.5 ml i.po.) caused a significant increase in eosinophil recruitment to the air pouch compared to saline (0.5 ml i.po.; eotaxin 5.3·1.1, saline 1.2·0.3 eosinophils×10$^5$; n=6, P<0.01 Mann-Whitney test). In further experiments 100 pmols kg$^{-1}$ IL-5 (i.v.) as well as 1 µg human eotaxin (i.po.) were used and measurements were made 6 h after administration of eotaxin. A control group treated with saline alone was also included in all experiments to give the baseline cell influx (sham challenge group).

Ovalbumin Challenge Procedure

The challenge dose of ovalbumin was determined from a series of pilot experiments in ovalbumin sensitized mice. In an initial experiment, Ovalbumin 1 and 10 but not 100 µg (0.5 ml, i.po.) was shown to cause a significant eosinophil recruitment compared with vehicle treated animals (0.5 ml saline, i.po.) after 24 h. As 10 µg Ovalbumin produced the most reproducible response (ovalbumin 6.4±1.1, saline 1.46±0.23 eosinophils×10$^5$; n=6, P<0.01, ANOVA with Dunnett's Test) this dose was subsequently used in a time course experiment. In this experiment mice received either saline or 10 μg ovalbumin (i.po.) and cell influx was assessed between 2-72 h after challenge. The 6 h time point was selected as eosinophil (as well as total cell) influx to the air pouch was maximal at this time (ovalbumin 5.4±1.4, saline 1.1±0.2 eosinophils× 10$^5$; n=5-6). In all subsequent experiments 10 μg ovalbumin (i.po.) was administered and measurements taken at 6 h. A control group challenged with saline alone was also included in all experiments to give the baseline cell influx (sham challenge group). Furthermore, mouse eotaxin levels were shown to be elevated following ovalbumin challenge (10 μg i.po.) in ovalbumin sensitized animals (saline control 93±12, ovalbumin challenge 3539±372 μg ml$^{-1}$; n=8-9, P<0.001, Mann-Whitney test).

Drug Administration

Systemic IgG antibody treatments (CAT-213, CAT-001 [null IgG control], or anti-mouse eotaxin IgG1 (R&D Systems)) were i.v. 30 min before administration of human eotaxin or ovalbumin. Local intra-air pouch treatments with CAT-212, CAT-171 [null scFv control] or CAT-213 were concomitant with administration of human eotaxin or ovalbumin. Vehicle control groups were included in all antibody experiments and these mice received PBS. All i.v. injections were made via the tail vein in a volume of 100 μl and all i.po. injections were made in a total volume of 0.5 ml.

Quantification of Results

Mice were killed prior to lavage by either $CO_2$ asphyxiation or, when plasma samples were required, an overdose of sodium pentobarbitone was followed by cardiac puncture. The air pouches were lavaged with ice cold PBS (1 ml; without calcium or magnesium; Sigma) containing 5 U ml$^{-1}$ heparin and stored on ice. An aliquot (10 μl) of lavage fluid was removed for assessment of total cells (fast-read, disposable cell counter, Immune Systems Ltd) and a further sample containing 100,000 cells was taken for cytospin preparation. The remaining lavage fluid was centrifuged 1000 g for 5 min, the supernatant was then aliquoted and stored at B70° C. The cell pellet was resuspended and cytospins prepared, air dried and stained with Wrights stain for differential cell counting. In some instances the lavage supernatant was assayed for eotaxin by ELISA (R&D Systems).

All results shown are mean±SE. The cell influx data are expressed as the number of cell per air pouch or, for drug treatment, as % inhibition of eosinophil influx. % inhibition of eosinophil influx was calculated from cell number data for each treatment group with the following equation:

(Mean cell influx challenged [PBS control] group−
Cell influx test mouse)×100(Mean cell influx
challenged [PBS control] group B Mean cell
influx sham challenge group)

The mean±SE was then calculated for each treatment group.

Most raw data were statistically analyzed with either ANOVA with Dunnett's. Students unpaired t test or Mann-Whitney tests were also used. All statistical analysis was performed using the Instat software and differences between mean values were taken as significant when P<0.05.

Results

Effect of CAT-212 or CAT-213 in mice treated with eotaxin i.po.

Figure 10:
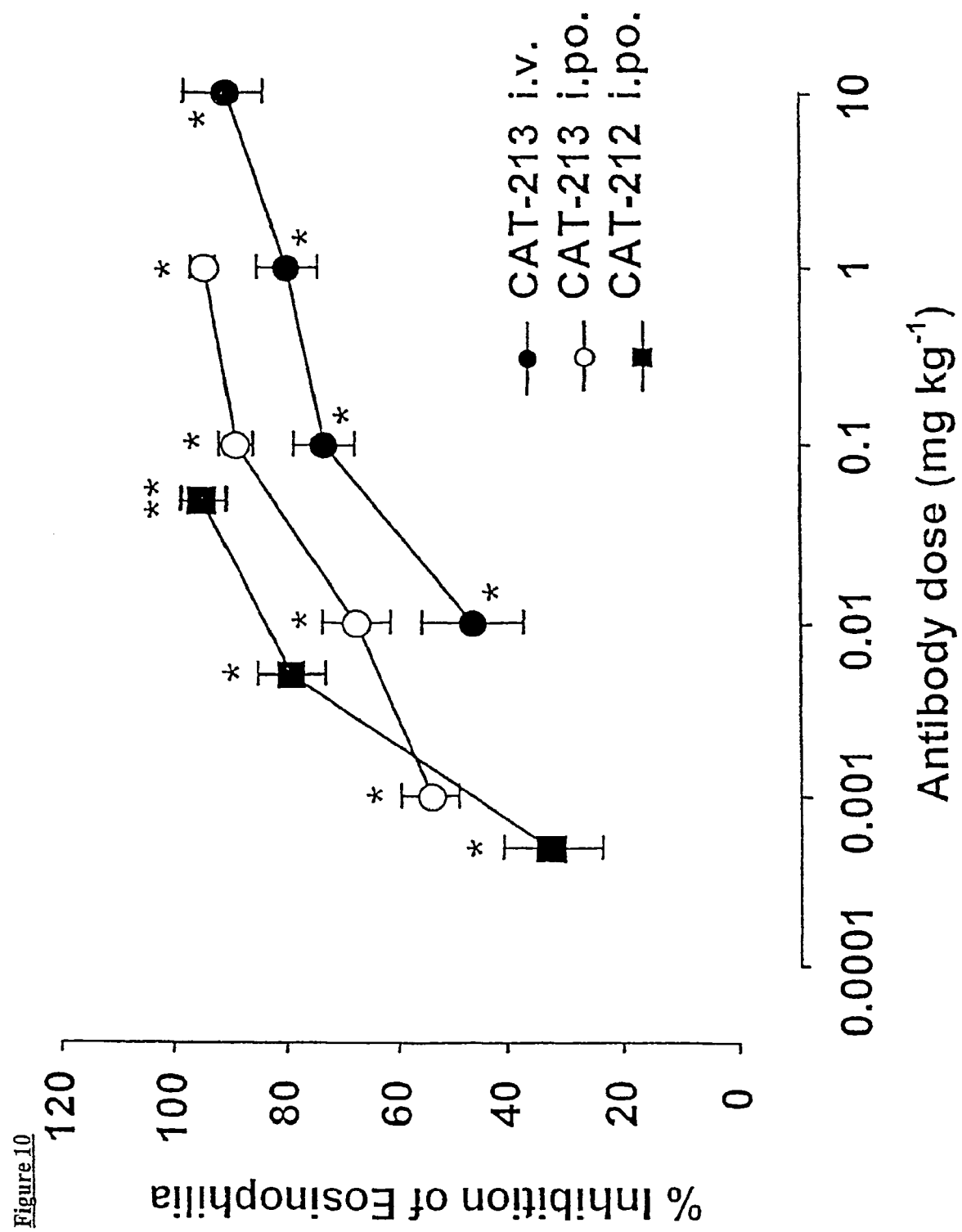
FIG. 10 shows the effect of CAT-212 and CAT-213 on human eotaxin induced eosinophil recruitment to the air pouch on ovalbumin sensitized mice treated with IL-5. CAT-212 was administered i.po. whereas CAT-213 was administered both i.po. and i.v. in separate experiments. The effect of antibody treatment was statistically evaluated by performing one way ANOVA with Dunnett's test using the differential cell count data. * $P<0.05$, ** $P<0.01$ compared to human eotaxin challenged PBS control animals (=0% inhibition; n 7-8 mice). Each point represents the mean value and the vertical bars show SE. CAT-213 or CAT-212 administered locally to the air pouch caused a dose-related inhibition of eosinophilia. CAT-213 given systemically also significantly inhibited eosinophil chemotaxis.
Figure 11:
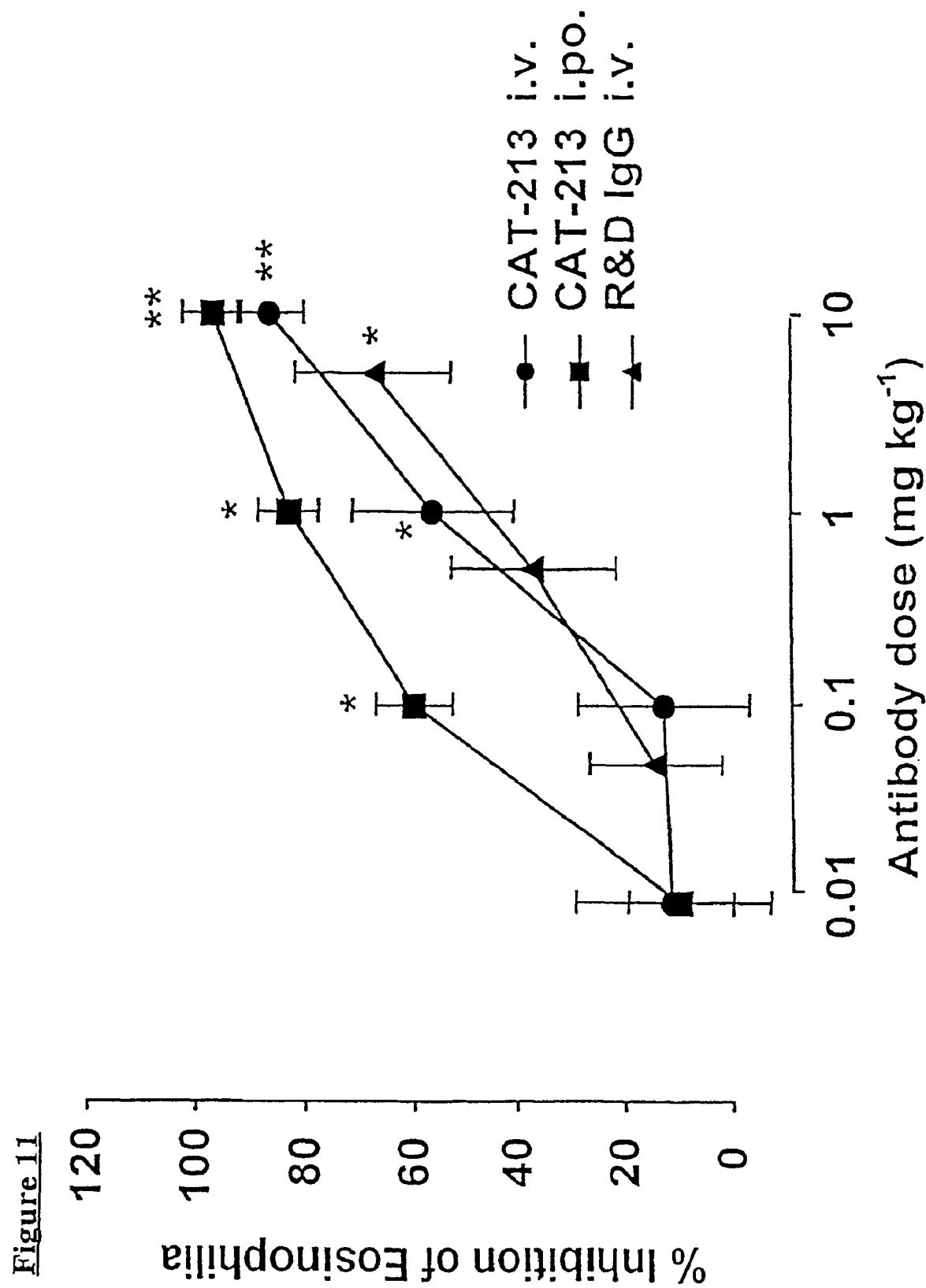
FIG. 11 illustrates the effect of CAT-213 on ovalbumin induced eosinophil recruitment to the air pouch on ovalbumin sensitized mice. CAT-213 was administered both i.po. and i.v. in separate experiments. The effect of antibody treatment was statistically evaluated by performing one way ANOVA with Dunnett's test using the differential cell count data. * $P<0.05$, ** $P<0.01$ compared to ovalbumin challenged PBS control animals (=0% inhibition; n=7-8 mice). Each point represents the mean value and the vertical bars show SE. CAT-213 administered locally to the air pouch or given systemically caused a potent dose-related inhibition of eosinophilia. The effect of i.v. administration of anti-mouse eotaxin IgG2A (R&D Systems mAb) on eosinophil recruitment are shown for comparison.

CAT-212 (0.0005, 0.005 & 0.05 mg kg$^{-1}$ i.po.) significantly attenuated the eosinophilia (32, 79 and 95% inhibition, respectively; n=8) caused by human eotaxin (1 g; i.po) in IL-5 treated, ovalbumin sensitized mice (FIG. 10). CAT-171 null control scFv (0.05 g kg$^{-1}$ i.po.) had no effect on eosinophil recruitment (−5·15% inhibition; n=8).

CAT-213 (0.001, 0.01, 0.1 & 1 mg kg$^{-1}$, n=7-8) administered i.po. concurrently with human eotaxin (1 μg, i.po) caused a potent doseBrelated inhibition of eosinophilia (FIG. 10).

All doses of CAT-213 were effective and maximum inhibition of 94% was observed with CAT-213 at 1 μg kg$^{-1}$. CAT-001 1 μg kg$^{-1}$ had little effect on cell influx (7·1% inhibition, n=8).

CAT-213 (0.01, 0.1, 1 & 10 mg kg$^{-1}$) administered i.v. 30 min before i.po. injection of human eotaxin (1 μg) caused a significant dose-dependent inhibition (46, 73, 79 & 91%, respectively, n=8) of eosinophil recruitment in IL-5 treated, ovalbumin sensitised mice (FIG. 10). CAT-001 control IgG4 (10 mg kg$^{-1}$) did not significantly affect eosinophil recruitment (8±1% inhibition, n=8).

Thus, intra-air pouch administration of CAT-213 is equipotent with CAT-212 in its ability prevent eosinophilia in vivo ($ED_{90}$ for both CAT-213 and CAT-212 is approximately $1×10^{-9}$ mols kg$^{-1}$) CAT-213 and CAT-212 block eosinophilia in vivo by neutralising human eotaxin; these antibodies have previously been shown to have a similar neutralising potency against human eotaxin when compared in the in vitro chemotaxis assay (see Example 12). CAT-213 also prevents eosinophil recruitment following i.v. administration (CAT-212 was not tested i.v.). However, CAT-213 is a more potent inhibitor of human eotaxin induced eosinophilia when given locally (CAT-213 i.po. is approximately 10 fold more potent compared with i.v. administration; FIG. 10).

Effect of CAT-213 in ovalbumin i.po. treated animals CAT-213 (0.01, 0.1, 1 & 10 mg kg$^{-1}$, n=7B8) i.po. dose-dependently inhibited eosinophil recruitment induced by ovalbumin. CAT-213 and ovalbumin were administered concurrently. CAT-213 0.1 mg kg$^{-1}$ and 10 mg kg$^{-1}$ caused 60% and 97% inhibition, respectively. CAT-213 i.po. also inhibited mononuclear cell influx to the air pouch, however, neutrophil recruitment was not significantly affected (Table 2). CAT-001 10 mg kg$^{-1}$ i.po. had little effect on cell influx (inhibition of eosinophil influx was B20±18%, n=8).

CAT-213 administered i.v. significantly inhibited eosinophil recruitment induced by ovalbumin (i.po.). CAT-213 (0.01, 0.1, 1 & 10 mg kg$^{-1}$ i.v., n 8) given 30 min before ovalbumin blocked eosinophilia at 6 h. 1 and 10 mg kg$^{-1}$ caused a significant inhibition of eosinophil recruitment by 56 and 85%, respectively. CAT-213 0.01 and 0.1 mg kg$^{-1}$ as well as CAT-001 (null antibody control) 10 mg kg$^{-1}$ were inactive (FIG. 19; CAT-001 inhibition 14·14%, n=8). CAT-213 i.v. (but not CAT-001) caused a dose-related inhibition of ovalbumin induced neutrophil and mononuclear cell recruitment to the air-pouch (Table 2).

Again, the data above provides indication that CAT-213 is a more potent inhibitor of eosinophilia when given locally to the air pouch (approximately 10 fold more potent than i.v. administration; FIG. 19). However, systemic (i.v.), but not local (i.po.) administration of CAT-213 has the ability to block neutrophil influx. Both systemic and local administration of CAT-213 can inhibit mononuclear cell chemotaxis.

In a separate experiment, the effects of systemic (i.v.) administration of anti-mouse eotaxin IgG2A (R&D Systems) were investigated in ovalbumin (i.po.) challenged mice to provide comparative data. Anti-mouse eotaxin (0.05, 0.5 & 5 mg kg$^{-1}$, n=7-8) caused a dose-related inhibition of eosinophil recruitment (14, 37 & 67%, respectively). Thus CAT-213 and the anti-mouse eotaxin IgG2A produced a similar inhibition of eosinophil chemotaxis both in magnitude of response and potency (FIG. 19).

Summary

In summary, the human anti-eotaxin antibodies, CAT-212 (scFv) and CAT-213 (IgG4) potently block eosinophilia in an in vivo model of allergic inflammation. CAT-213 is effective when given both locally and systemically. Systemic administration of CAT-213 has the additional action of blocking neutrophil as well as mononuclear cell chemotaxis. These data are consistent with an action of CAT-213 and CAT-212 in blocking the biological response to eotaxin in vivo.

EXAMPLE 15

Neutralisation Potency of CAT-213 in an Eotaxin-Mediated Chemotaxis Assay Using L1.2 CCR-3 Transfected Cells: Rhesus Monkey and Mouse Eotaxin The ability of CAT-213 to neutralise rhesus monkey and mouse eotaxin was assessed in the chemotaxis assay, essentially as described in Example 2.

Assay Protocol

The assay protocol followed was essentially the same as that described for Example 2. Chemotaxis was induced with either rhesus monkey eotaxin or murine eotaxin. Rhesus monkey (125 ng/ml) or murine (50 ng/ml) eotaxin were incubated in the lower chamber of a Transwell culture system prior to the addition of $1\times10^6$ or $2\times10^6$ L1.2-CCR3 cells, respectively to the upper chamber of the Transwell. Migrated cells were quantitated by FACS analysis and were counted at a high flow rate for 1 minute.

Results

Figure 12:
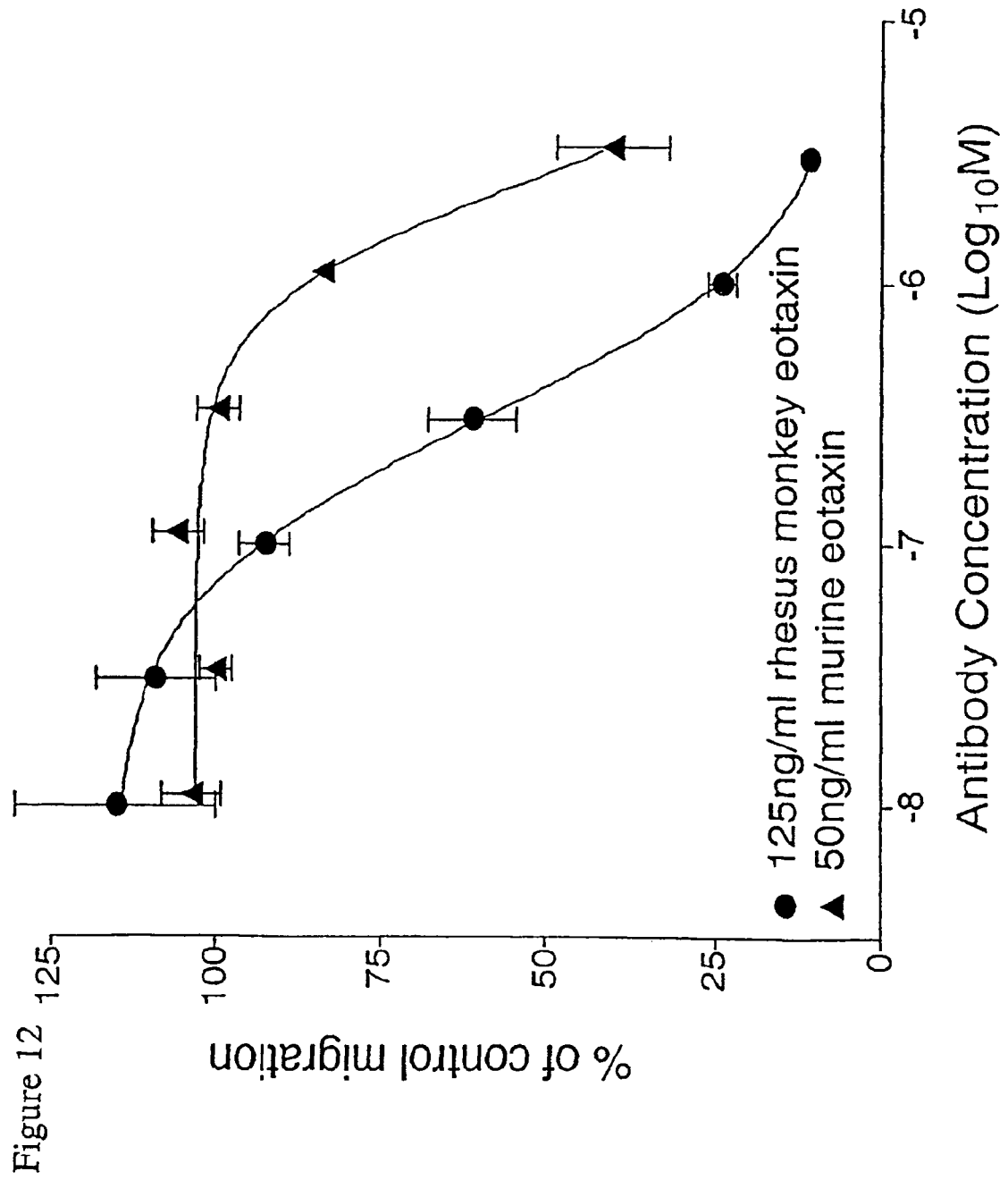
FIG. 12 illustrates the effect of CAT-213 on rhesus monkey eotaxin- and murine eotaxin-induced chemotaxis of L1.2-CCR3 cells. Data are expressed as mean±SEM from at least 3 experiments performed in triplicate or duplicate, respectively.

CAT-213 inhibited rhesus monkey and mouse eotaxin-mediated chemotaxis of L1.2-CCR3 cells with geometric mean $IC_{50}$ and 95% confidence interval values of $3.03\times10^{-7}$ M ($1.01\times10^{-7}$, $9.01\times10^{-7}$ M) and $2.63\times10^{-6}$ M ($1.30\times10^{-6}$, $5.34\times10^{-6}$ M), respectively (FIG. 12). The data represent at least 3 experiments performed in triplicate and duplicate, respectively.

EXAMPLE 16

Neutralisation Potency of CAT-213 in an Eotaxin-Mediated Chemotaxis Assay Using Human Eosinophils The chemotaxis assay is a relevant in vitro assay system as it assesses the ability of eotaxin to chemoattract cells expressing CCR3. These experiments are of increased physiological relevance as in this case the CCR3-expressing cells are human eosinophils obtained directly from blood.

Preparation of Eosinophils

Eosinophils were isolated from heparinized peripheral blood of atopic, non-asthmatic donors with no symptoms of allergic disease. Blood was mixed with ⅕ volume dextran solution (6% w/v in saline) and erythrocytes were allowed to sediment for 45 minutes at room temperature. The erythrocyte-depleted plasma was layered onto Lymphoprep® and centrifuged at 800 g for 25 minutes at 20° C. to separate mononuclear cells from granulocytes.

Granulocyte pellets were depleted of residual erythrocytes via two rounds of hypotonic lysis, after which neutrophils were labelled with anti-CD16-coated superparamagnetic microbeads (MACS, Miltenyi Biotec; 2 µl beads per $3\times10^6$ granulocytes) by a 30-minute incubation at 0° C. The cells were then loaded onto a 10 ml steel wool column in a strong magnetic field and the unlabelled cells eluted with four column volumes of ice-cold labelling buffer (PBS, $2\times10^{-3}$ M EDTA, 0.5% w/v bovine serum albumin). The eluted cells were routinely >95% eosinophils.

Assay Protocol

Eosinophils were resuspended in HBSS supplemented with $1\times10^{-2}$ M HEPES and 0.3% w/v BSA, and incubated for at least 45 min at 37° C./5% $CO_2$ prior to use in chemotaxis assays. Samples (medium or $1\times10^{-8}$ M human eotaxin, plus or minus CAT-213 or CAT-001 (control antibody)) were added to the lower wells of 48-well microchemotaxis chambers. Polyvinylpyrrolidone (PVP)-free polycarbonate membrane filters (8-µm pore size) were placed between the lower and upper wells and the chambers were incubated for 30 minutes at 37° C./5% $CO_2$. Cells were then added to the upper wells and the chambers incubated for a further 60 minutes at 37° C./5% $CO_2$. At the end of this period, non-migrating cells were scraped from the upper surface of the filters; the filters were dried, fixed in methanol and stained using May-Grünwald/Giemsa. Migrated cells were counted in 5 high-power (×400) fields for each sample.

Results

Figure 13:
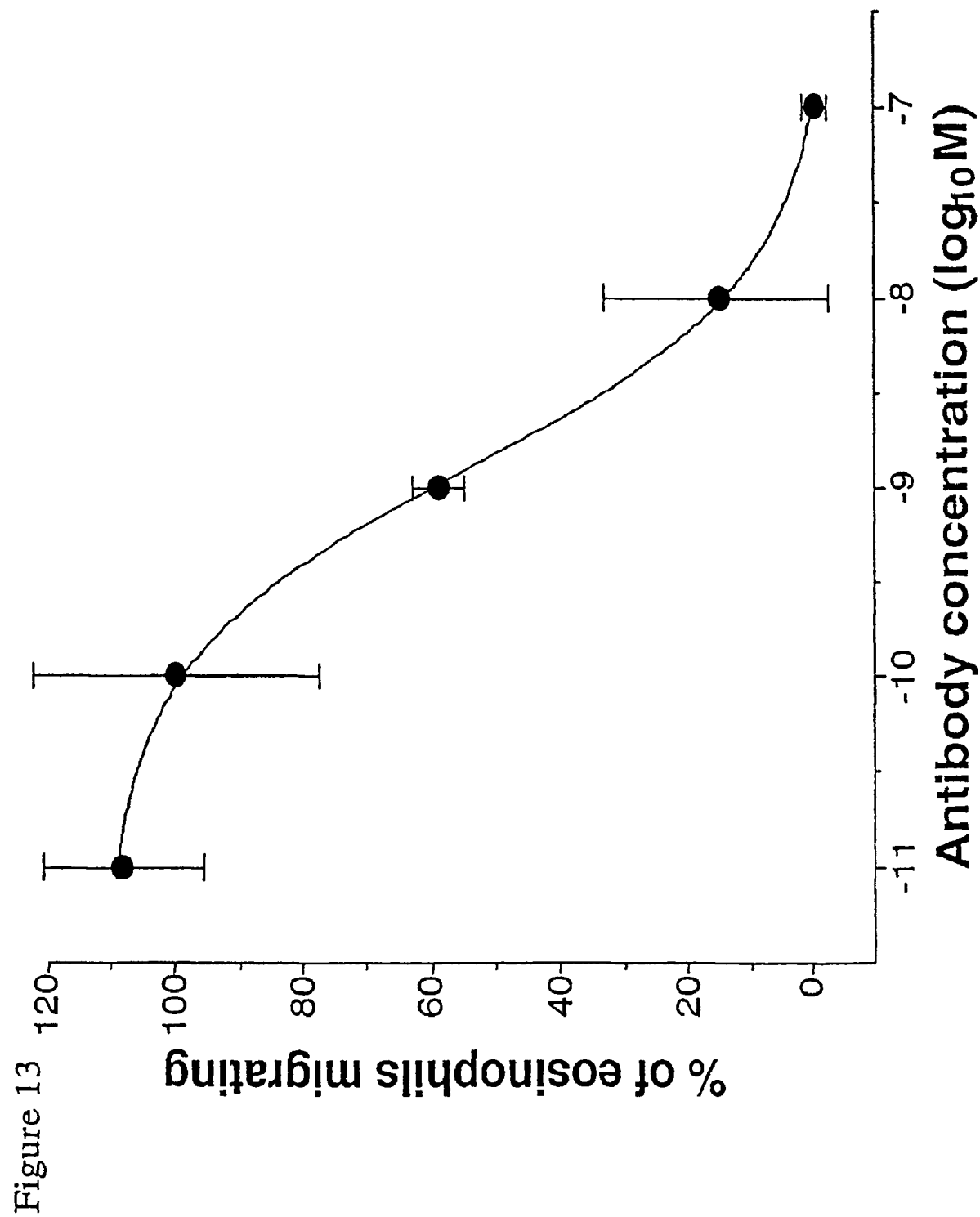
FIG. 13 shows neutralisation by CAT-213 of human eotaxin-induced chemotaxis of human peripheral eosinophils. Data are expressed as mean±SEM from 3 experiments, performed with triplicate points.

The results of three separate experiments performed with triplicate points are shown in FIG. 13 (mean±SEM). CAT-213 inhibited eotaxin-mediated chemotaxis of human eosinophils with a geometric mean $IC_{50}$ and 95% confidence intervals of $1.53\times10^{-9}$ M ($3.09\times10^{-11}$, $7.54\times10^{-8}$ M). CAT-001 (the control antibody) did not affect chemotaxis. Therefore, CAT-213 neutralises eotaxin-induced chemotaxis of human eosinophils.

EXAMPLE 17

Neutralisation Potency of CAT-213 in an Eotaxin-Mediated Eosinophil Shape Change Assay Shape change is a requisite process in chemotaxis and can be taken as evidence of a migratory response, to come. In order for eosinophils to move from the circulation into the tissues in response to an eotaxin gradient (chemotaxis), reorganisation of cytoskeletal elements must occur. This reorganisation is associated with specific changes in cell morphology which can be visualised on a flow cytometer as changes in forward scatter (FSC). The assay used in this example uses a method described by Sabroe et al (1999).

Assay Protocol

Experiments were performed using granulocyte preparations which were obtained as follows. Peripheral blood was taken into syringes containing EDTA (150 µl 0.5M EDTA per 10 ml blood) and the erythrocytes sedimented by addition of 1 ml of 6% dextran-T500 in 0.9% saline per 10 ml of blood. Sedimentation was allowed to occur for 40 minutes at room temperature. The erythrocyte-depleted plasma was then layered onto a discontinuous 70%-80% percoll gradient and centrifuged at 1137 g for 20 minutes at room temperature to separate mononuclear cells from granulocytes. The resultant granulocyte layer was washed in PBS and then pelleted at 306 g for 5 minutes at room temperature. The cell pellet was then resuspended in shape change buffer (PBS, $1\times10^{-3}$ M $CaCl_2$, $1\times10^{-3}$ M $MgCl_2$, $1\times10^{-2}$ M HEPES, $1\times10^{-2}$ M glucose, 0.1% BSA, pH 7.3). Cells were then incubated at 37° C. for 30 min.

$3\times10^{-9}$ M eotaxin or buffer, plus or minus CAT-213 or CAT-001 (control) were added to polypropylene flow cytometer tubes in a volume of 300 µl. $5\times10^5$ cells (in 100 µl) were added to each tube. Tubes were then immediately incubated at 37° C. for 7 minutes before being transferred to an ice water bath. Finally, 25 µl Cellfix buffer (10×) was added and individual tubes were read on a flow cytometer. Eosinophils were identified by their autofluorescence in the FL2 channel. FSC was then assessed.

Results

Figure 14:
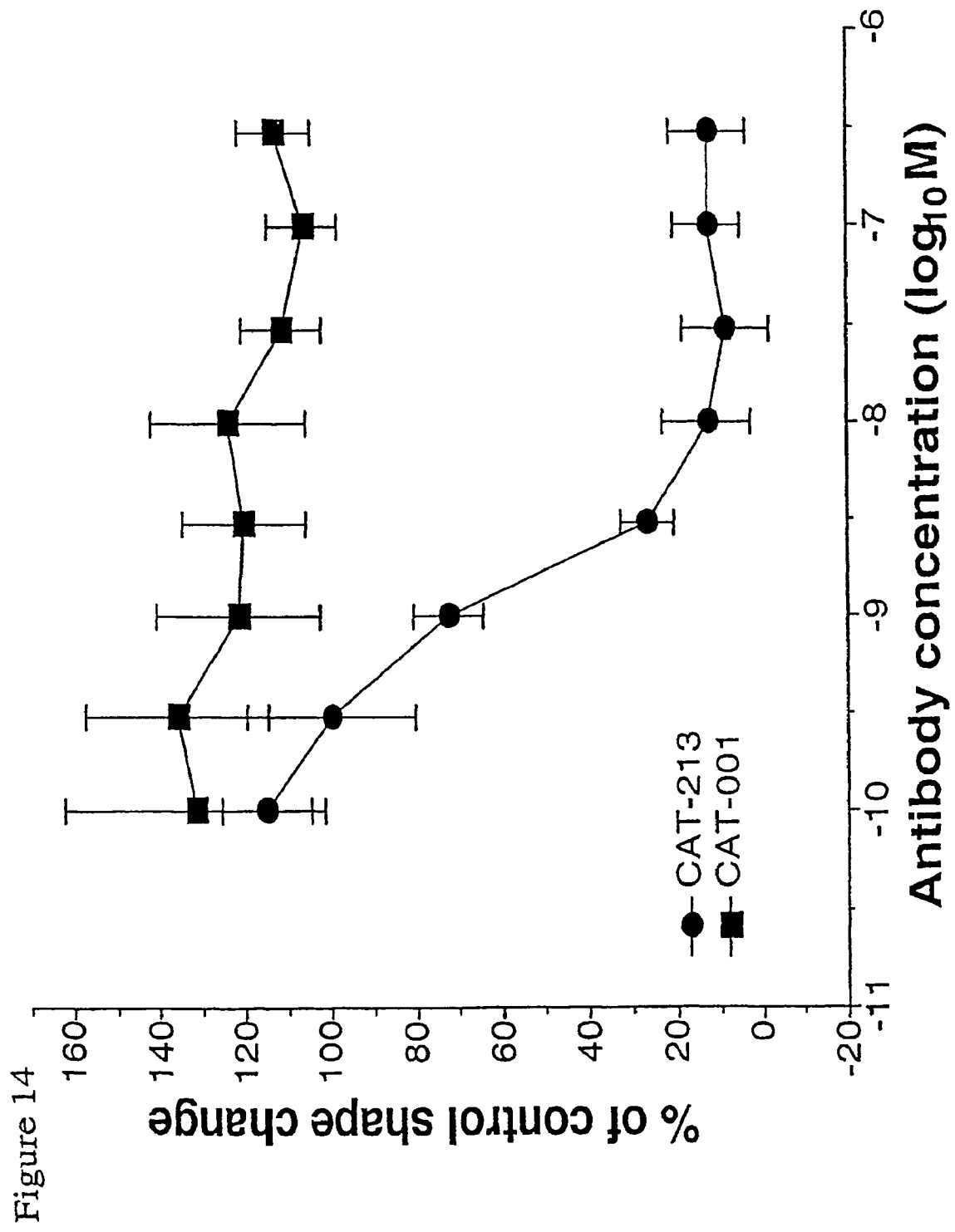
FIG. 14 shows that CAT-213 inhibited eotaxin-mediated shape change of human eosinophils. CAT-001 (the control antibody) was inactive. Data are expressed as mean±SEM from 5 experiments performed with duplicate points.

The results of this assay are shown in FIG. 14. CAT-213 inhibited shape change evoked in human eosinophils by human eotaxin, with a geometric mean $IC_{50}$ and 95% confidence interval of $7.14 \times 10^{-10}$M ($2.07 \times 10^{-10}$, $2.44 \times 10^{-9}$M). CAT-001 did not affect eotaxin induced shape change. Data are expressed as mean±SEM from 5 experiments performed with duplicate points, with cells from separate donors.

REFERENCES

Brown et al. 1998. Clinical Experimental Immunology, 114, 137-146.
Collins et al. 1995. J. Exp. Med, 182, 1169.
Combadiere et al. 1995. Journal of Biological Chemistry, 270, 16491-16494.
Cook et al. 1998. Allergy and Asthma Proceedings, 19, 15-22.
Das et al. 1997. Br J Pharmacol, 121, 97-104.
Daugherty et al. 1996. Journal of Experimental Medicine 183, 2349-2354.
Elsner et al. 1996. European Journal of Immunology, 26, 1919-1925.
Forssmann et al. 1997. Journal of Experimental Medicine, 185, 2171-2176.
Gao et al. 1996. Biochem. Biophys. Res. Comm. 223, 679-684.
Garcia-Zepeda et al. 1996. Nature Medicine, 2, 449-456.
Gonzalo et al. 1996. Journal of Clinical Investigation, 98, 2332-2345.
Griffiths-Johnson et al. 1993. Biochemical and Biophysical Research Communications, 197, 1167-1172.
He J, Chen Y, Farzan et al, 1997. CCR3 and CCr5 are co-receptors for HIV-1 infection of microglia. Nature, 385, 645-647.
Humbles et al. 1997. Journal of Experimental Medicine, 186, 601-612.
Jose et al. 1994b. Biochemical and Biophysical Research Communications, 205, 788-794.
Jose et al. 1994a. Journal of Experimental Medicine, 179, 881-887.
Kitaura et al. 1996. Journal of Biological Chemistry, 271, 7725-7730.
Kitaura et al, 1999. Journal of Biological Chemistry, 274, 27975-27980.
Li et al. 1997. European Respiration Journal, 10, 1946-1954.
Luster 1998. New Eng. J. Med. 338, 436-445.
Mattoli et al. 1997. Biochemical and biophysical research communications, 236, 299-301.
McCafferty et al. 1990. Nature, 348. 552-554.
Nakajima et al. 1998. FEBS Letters, 434, 226-230.
Osbourn et al. 1996. Immunotechnology 2, 181-196.
Ponath et al. 1996a. Journal of Clinical Investigations. 97, 604-612.
Ponath et al. 1996b. Journal of Experimental Medicine, 183, 2437-2448.
Rothenberg 1998. New Eng. J. Med. 338, 1592-1600.
Rothenberg 1995b. Proceeding of the National Academy of Sciences, 92, 8960-8964.
Rothenberg et al. 1995a. Journal of Experimental Medicine, 181, 1211-1216.
Rothenberg et al. 1997. Journal of Experimental Medicine, 185, 785-790.
Rubbert et al. 1998. Journal of Immunology, 160, 3933-3941.
Sabroe et al. 1998. J. Immunol. 161, 6139-6147.
Sabroe, I., et al., J Immunol, 1999. 162(5): p. 2946-55.
Sallusto et al. 1997. Science, 277, 2005-2007.
Sanz et al. 1998. Journal of Immunology, 160, 3569-3576.
Shinkai et al. 1999. Journal of Immunology, 163, 1602-1610.
Teixeira et al. 1997. Journal of Clinical Investigations, 100, 1657-1666.
Tenscher et al. 1996. Blood, 88, 3195-3199.
Tomlinson et al. 1995. The V-BASE sequence directory. MRC Centre for Protein Engineering, Cambridge, UK. http://www.mrc-cpe.cam.ac.uk
Uguccioni et al. 1997. Journal of Clinical Investigation, 100, 1137-1143.
Van Coillie et al. 1999. Cytokine and growth factor reviews, 10, 61-86.
Vaughan et al. 1996. Nature Biotechnology, 14, 309-314.
White et al. 1997. Journal of Leukocyte Biology, 62, 667-675.
Williams et al. 1998. Immunogenetics, 47, 178-180.
Yamada et al. 1997. Biochemical and Biophysical Research Communications, 231, 365-368.
Ying et al. 1997. European Journal of Immunology, 27, 3507-3516.

TABLE 1

| Test Antigen | Coating concentration (μg/ml) | Supplier |
|---|---|---|
| Human Eotaxin | 10 | Cambridge Bioscience |
| Mouse Eotaxin | 10 | Cambridge Bioscience |
| MIP-1α | 10 | Cambridge Bioscience |
| MCP-1 | 10 | Cambridge Bioscience |
| MCP-2 | 10 | Cambridge Bioscience |
| MCP-3 | 10 | Cambridge Bioscience |
| MCP-4 | 10 | Cambridge Bioscience |
| IL-1α | 1 | Cambridge Bioscience |
| IL-1β | 1 | Cambridge Bioscience |
| IL-5 | 1 | R&D Systems |
| IL-12 | 1 | Gift: from Genetics Institute |
| IL-18 | 1 | R&D Systems |
| TGF-β1 | 0.5 | ImmunoKontact |
| TGF-β2 | 0.5 | ImmunoKontact |
| TNFα | 10 | Gift: BASF Bio-Research Corporation |
| RANTES | 10 | Peprotech |

TABLE 2

The Effect of CAT-213 i.v. on Ovalbumin-induced Neutrophil and Mononuclear Cell Recruitment in Ovalbumin Sensitized Mice

| Treatment | Dose (mg kg$^{-1}$ i.v.) | Neutrophils (% Inhibition) | Mononuclear cells (% Inhibition) | n |
|---|---|---|---|---|
| CAT-213 | 0.01 | 9 ± 13 | −7 ± 18 | 8 |
|  | 0.1 | 37 ± 9 | 49 ± 23 | 8 |
|  | 1 | 41 ± 12* | 101 ± 30* | 8 |
|  | 10 | 61 ± 6** | 156 ± 12** | 8 |
| CAT-001 | 10 | 1 ± 10 | −3 ± 57 | 8 |

Mean±SE % inhibition values for the effect of CAT-213 or CAT-001 on neutrophil or mononuclear cell chemotaxis. The effect of antibody treatment was statistically evaluated by performing one way ANOVA with Dunnett's test using the differential cell count data. * $P<0.05$, ** $P<0.01$ compared to ovalbumin challenged PBS control animals. CAT-213 i.v. significantly inhibited neutrophil and mononuclear cell chemotaxis.

TABLE 3

List of primers used for conversion of CAT-212 to IgG format

| SEQ ID NO. | Primer |
|---|---|
| 11 | P10 |
| 12 | P11 |
| 13 | P24 |
| 14 | P34 |
| 15 | P36 |
| 16 | P37 |
| 17 | P109a |
| 18 | P110b |
| 19 | P113 |
| 20 | P132 |

The invention claimed is:

1. An isolated nucleic acid which comprises a nucleotide sequence encoding a specific binding member that binds human eotaxin, wherein said specific binding member comprises:

(i) an antibody VH domain comprising the VH CDR1 amino acid sequence provided in SEQ ID NO:5, the VH CDR2 amino acid sequence provided in SEQ ID NO:6, and the VH CDR3 amino acid sequence provided in SEQ ID NO:7; and (ii) an antibody VL domain comprising the VL CDR1 amino acid sequence provided in SEQ ID NO:8, the VL CDR2 amino acid sequence provided in SEQ ID NO:9, and the VL CDR3 amino acid sequence provided in SEQ ID NO:10.

2. The isolated nucleic acid of claim 1 wherein the VH domain comprises the amino acid sequence provided in SEQ ID NO:2.

3. The isolated nucleic acid of claim 2 wherein the VL domain comprises the amino acid sequence provided in SEQ ID NO:4.

4. The isolated nucleic acid of claim 3 wherein the binding member neutralizes eotaxin.

5. The isolated nucleic acid of claim 3 wherein the binding member comprises an scFv antibody molecule.

6. The isolated nucleic acid of claim 3 wherein the specific binding member comprises an antibody constant region.

7. The isolated nucleic acid of claim 3 wherein the specific binding member comprises a whole antibody.

8. The isolated nucleic acid of claim 3 wherein the specific binding member comprises an IgG4 constant region.

9. A host cell transformed with the nucleic acid of claim 3.

10. The isolated nucleic acid of claim 1 wherein the VL domain comprises the amino acid sequence provided in SEQ ID NO:4.

11. The isolated nucleic acid of claim 1 wherein the binding member neutralizes eotaxin.

12. The isolated nucleic acid of claim 1 wherein the binding member comprises an scFv antibody molecule.

13. The isolated nucleic acid of claim 1 wherein the specific binding member comprises an antibody constant region.

14. The isolated nucleic acid of claim 1 wherein the specific binding member comprises a whole antibody.

15. The isolated nucleic acid of claim 1 wherein the specific binding member comprises an IgG4 constant region.

16. A host cell transformed with the nucleic acid of claim 1.

17. An isolated nucleic acid which comprises a nucleotide sequence encoding a specific binding member that binds human eotaxin, wherein said specific binding member comprises an antibody VL domain comprising the VL amino acid sequence provided in SEQ ID NO:4.

18. An isolated nucleic acid which comprises a nucleotide sequence encoding a specific binding member that binds human eotaxin, wherein said specific binding member comprises an antibody VH domain comprising the VH amino acid sequence provided in SEQ ID NO:2.

* * * * *

SEQUENCE LISTING

<160> NUMBER OF SEQ ID NOS: 20

<210> SEQ ID NO 1
<211> LENGTH: 354
<212> TYPE: DNA
<213> ORGANISM: homo sapiens

<400> SEQUENCE: 1

```
caggtgcagc tggtgcaatc tggggggaggc gtggtccagc ctgggaggtc cctgagactc    60
tcctgtgcag cctctggatt caccttcagt agctatggca tgcactgggt ccgccaggct   120
ccaggcaagg ggctggagtg ggtggcagtt atatcatatg atggaagcat taaacattat   180
gcagactccg tgaagggccg attcaccatc tccagagaca attccaagaa cacgctgtat   240
ctgcaaatga acagcctgag aactgacgac acggctgtat attactgtgc gggagatacg   300
gactacgggg acatcgaccc gtggggtcag ggcaccatgg tgacggtctc gagt          354
```

<210> SEQ ID NO 2
<211> LENGTH: 118
<212> TYPE: PRT
<213> ORGANISM: homo sapiens

<400> SEQUENCE: 2

```
Gln Val Gln Leu Val Gln Ser Gly Gly Gly Val Val Gln Pro Gly Arg
1               5                   10                  15
Ser Leu Arg Leu Ser Cys Ala Ala Ser Gly Phe Thr Phe Ser Ser Tyr
            20                  25                  30
Gly Met His Trp Val Arg Gln Ala Pro Gly Lys Gly Leu Glu Trp Val
        35                  40                  45
Ala Val Ile Ser Tyr Asp Gly Ser Ile Lys His Tyr Ala Asp Ser Val
    50                  55                  60
Lys Gly Arg Phe Thr Ile Ser Arg Asp Asn Ser Lys Asn Thr Leu Tyr
65                  70                  75                  80
Leu Gln Met Asn Ser Leu Arg Thr Asp Asp Thr Ala Val Tyr Tyr Cys
                85                  90                  95
Ala Gly Asp Thr Asp Tyr Gly Asp Ile Asp Pro Trp Gly Gln Gly Thr
            100                 105                 110
Met Val Thr Val Ser Ser
        115
```

<210> SEQ ID NO 3
<211> LENGTH: 326
<212> TYPE: DNA
<213> ORGANISM: homo sapiens

<400> SEQUENCE: 3

```
acatccagat gacccagtct ccatcttccg tgtctgcatc tgtaggagac agagtcacca    60
```

```
tcacttgtcg ggcgagtcag gatattagca gctggttagc ctggtatcag cagaaacctg      120
ggaaagcccc taagctcctg atctatgctg catccagttt gcaaagtggg gtcccatcaa      180
ggttcagcgg cagtggatct gggacagatt tcactctcac catcagcagc ctgcagcctg      240
aagattttgc aacttactat tgtcagcagg ctagcagttt ccccctcgatc accttcggcc     300 aagggacacg actggagatt aaacgt                                           326
```

<210> SEQ ID NO 4
<211> LENGTH: 109
<212> TYPE: PRT
<213> ORGANISM: homo sapiens

<400> SEQUENCE: 4

```
Asp Ile Gln Met Thr Gln Ser Pro Ser Ser Val Ser Ala Ser Val Gly
1               5                   10                  15

Asp Arg Val Thr Ile Thr Cys Arg Ala Ser Gln Asp Ile Ser Ser Trp
            20                  25                  30

Leu Ala Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Ser Ser Phe Pro Ser
                85                  90                  95

Ile Thr Phe Gly Gln Gly Thr Arg Leu Glu Ile Lys Arg
            100                 105
```

<210> SEQ ID NO 5
<211> LENGTH: 5
<212> TYPE: PRT
<213> ORGANISM: homo sapiens

<400> SEQUENCE: 5

```
Ser Tyr Gly Met His
1               5
```

<210> SEQ ID NO 6
<211> LENGTH: 17
<212> TYPE: PRT
<213> ORGANISM: homo sapiens

<400> SEQUENCE: 6

```
Val Ile Ser Tyr Asp Gly Ser Ile Lys His Tyr Ala Asp Ser Val Lys
1               5                   10                  15

Gly
```

<210> SEQ ID NO 7
<211> LENGTH: 9
<212> TYPE: PRT
<213> ORGANISM: homo sapiens

<400> SEQUENCE: 7

```
Asp Thr Asp Tyr Gly Asp Ile Asp Pro
1               5
```

<210> SEQ ID NO 8
<211> LENGTH: 11
<212> TYPE: PRT
<213> ORGANISM: homo sapiens

```
<400> SEQUENCE: 8

Arg Ala Ser Gln Asp Ile Ser Ser Trp Leu Ala
1               5                   10

<210> SEQ ID NO 9
<211> LENGTH: 7
<212> TYPE: PRT
<213> ORGANISM: homo sapiens

<400> SEQUENCE: 9

Ala Ala Ser Ser Leu Gln Ser
1               5

<210> SEQ ID NO 10
<211> LENGTH: 10
<212> TYPE: PRT
<213> ORGANISM: homo sapiens

<400> SEQUENCE: 10

Gln Gln Ala Ser Ser Phe Pro Ser Ile Thr
1               5                   10

<210> SEQ ID NO 11
<211> LENGTH: 30
<212> TYPE: DNA
<213> ORGANISM: Artificial Sequence
<220> FEATURE:
<223> OTHER INFORMATION: Primer

<400> SEQUENCE: 11
ctaagcttac tgagcacaca ggacctcacc                               30

<210> SEQ ID NO 12
<211> LENGTH: 35
<212> TYPE: DNA
<213> ORGANISM: Artificial Sequence
<220> FEATURE:
<223> OTHER INFORMATION: Primer

<400> SEQUENCE: 12
aattttcgaa ctacagttac tgagcacaca ggacc                         35

<210> SEQ ID NO 13
<211> LENGTH: 21
<212> TYPE: DNA
<213> ORGANISM: Artificial Sequence
<220> FEATURE:
<223> OTHER INFORMATION: Primer

<400> SEQUENCE: 13
ggaggtgctc ctggagcagg g                                        21

<210> SEQ ID NO 14
<211> LENGTH: 29
<212> TYPE: DNA
<213> ORGANISM: Artificial Sequence
<220> FEATURE:
<223> OTHER INFORMATION: Primer

<400> SEQUENCE: 14
ctgttccttt ccatgggtct tttctgcag                                29

<210> SEQ ID NO 15
<211> LENGTH: 27
<212> TYPE: DNA
```

```
<213> ORGANISM: Artificial Sequence
<220> FEATURE:
<223> OTHER INFORMATION: Primer

<400> SEQUENCE: 15
ttccatgggt cttttctgca gtcaccg                                        27

<210> SEQ ID NO 16
<211> LENGTH: 27
<212> TYPE: DNA
<213> ORGANISM: Artificial Sequence
<220> FEATURE:
<223> OTHER INFORMATION: Primer

<400> SEQUENCE: 16
tatggctgat taatgatcaa tgaattc                                        27

<210> SEQ ID NO 17
<211> LENGTH: 45
<212> TYPE: DNA
<213> ORGANISM: Artificial Sequence
<220> FEATURE:
<223> OTHER INFORMATION: Primer

<400> SEQUENCE: 17
tttggatatc tctccacagg tgtccactcg gacatccaga tgacc                    45

<210> SEQ ID NO 18
<211> LENGTH: 37
<212> TYPE: DNA
<213> ORGANISM: Artificial Sequence
<220> FEATURE:
<223> OTHER INFORMATION: Primer

<400> SEQUENCE: 18
cggccaaggg acacgactgg agattaaacg tacggta                             37

<210> SEQ ID NO 19
<211> LENGTH: 54
<212> TYPE: DNA
<213> ORGANISM: Artificial Sequence
<220> FEATURE:
<223> OTHER INFORMATION: Primer

<400> SEQUENCE: 19
tttggatatc tctccacagg tgtccactcc caggtgcagc tggtgcaatc tggg          54

<210> SEQ ID NO 20
<211> LENGTH: 46
<212> TYPE: DNA
<213> ORGANISM: Artificial Sequence
<220> FEATURE:
<223> OTHER INFORMATION: Primer

<400> SEQUENCE: 20
atgggccctt ggtggaagca ctcgagaccg tcaccatggt gccctg                   46
```